United States Patent
Girard et al.

(10) Patent No.: US 9,867,694 B2
(45) Date of Patent: Jan. 16, 2018

(54) RADIALLY COLLAPSIBLE FRAME FOR A PROSTHETIC VALVE AND METHOD FOR MANUFACTURING SUCH A FRAME

(71) Applicant: JENAVALVE TECHNOLOGY, INC., Irvine, CA (US)

(72) Inventors: Michael J. Girard, Lino Lakes, MN (US); Martin Schlun, Munich (DE)

(73) Assignee: JenaValve Technology Inc., Irvine, CA (US)

(*) Notice: Subject to any disclaimer, the term of this patent is extended or adjusted under 35 U.S.C. 154(b) by 9 days.

(21) Appl. No.: 14/914,313

(22) PCT Filed: Jul. 23, 2014

(86) PCT No.: PCT/EP2014/065817
§ 371 (c)(1),
(2) Date: Feb. 25, 2016

(87) PCT Pub. No.: WO2015/028209
PCT Pub. Date: Mar. 5, 2015

(65) Prior Publication Data
US 2016/0213465 A1    Jul. 28, 2016

(30) Foreign Application Priority Data
Aug. 30, 2013  (EP) ..................................... 13182346

(51) Int. Cl.
*A61F 2/24*    (2006.01)
(52) U.S. Cl.
CPC .......... *A61F 2/2409* (2013.01); *A61F 2/2418* (2013.01); *A61F 2/2469* (2013.01);
(Continued)
(58) Field of Classification Search
CPC ......... A61F 2/24; A61F 2/2448; A61F 2/2418
(Continued)

(56) References Cited

U.S. PATENT DOCUMENTS

| 3,755,823 A | 9/1973 | Hancock |
| 4,485,816 A | 12/1984 | Krumme |

(Continued)

FOREIGN PATENT DOCUMENTS

| AU | 2006308187 A1 | 5/2007 |
| AU | 2006310681 A1 | 5/2007 |

(Continued)

OTHER PUBLICATIONS

International Search Report for PCT/EP2014/065817, dated Jan. 7, 2015 (5 pages).

(Continued)

*Primary Examiner* — Suzette J Gherbi
(74) *Attorney, Agent, or Firm* — Bookoff McAndrews, PLLC

(57) ABSTRACT

The present invention relates to a radially collapsible frame (1) for a prosthetic valve, the frame (1) comprising an outflow end region (3) at a proximal end of the frame (1) and an inflow end region (2) at a distal end of the frame (1), opposite to the outflow end region (3). The frame (1) further includes at least two radially spaced commissure attachment regions (10, 10', 10") and a cell structure (30), composed of a plurality of lattice cells being arranged radially around a flow axis of the frame (1) and connecting the at least two commissure attachment regions (10, 10', 10"). Finally, at least one anchoring/positioning arch (20, 20', 20") is provided, wherein said at least one anchoring/positioning arch (20, 20', 20") radially overlaps the cell structure (30) at least partially. In order to form the inventive frame from as a single piece, the invention further relates to a method comprising bending the at least one anchoring/positioning arch (20, 20', 20") towards the cell structure (30) of the frame (1).

27 Claims, 7 Drawing Sheets

Figure 1:
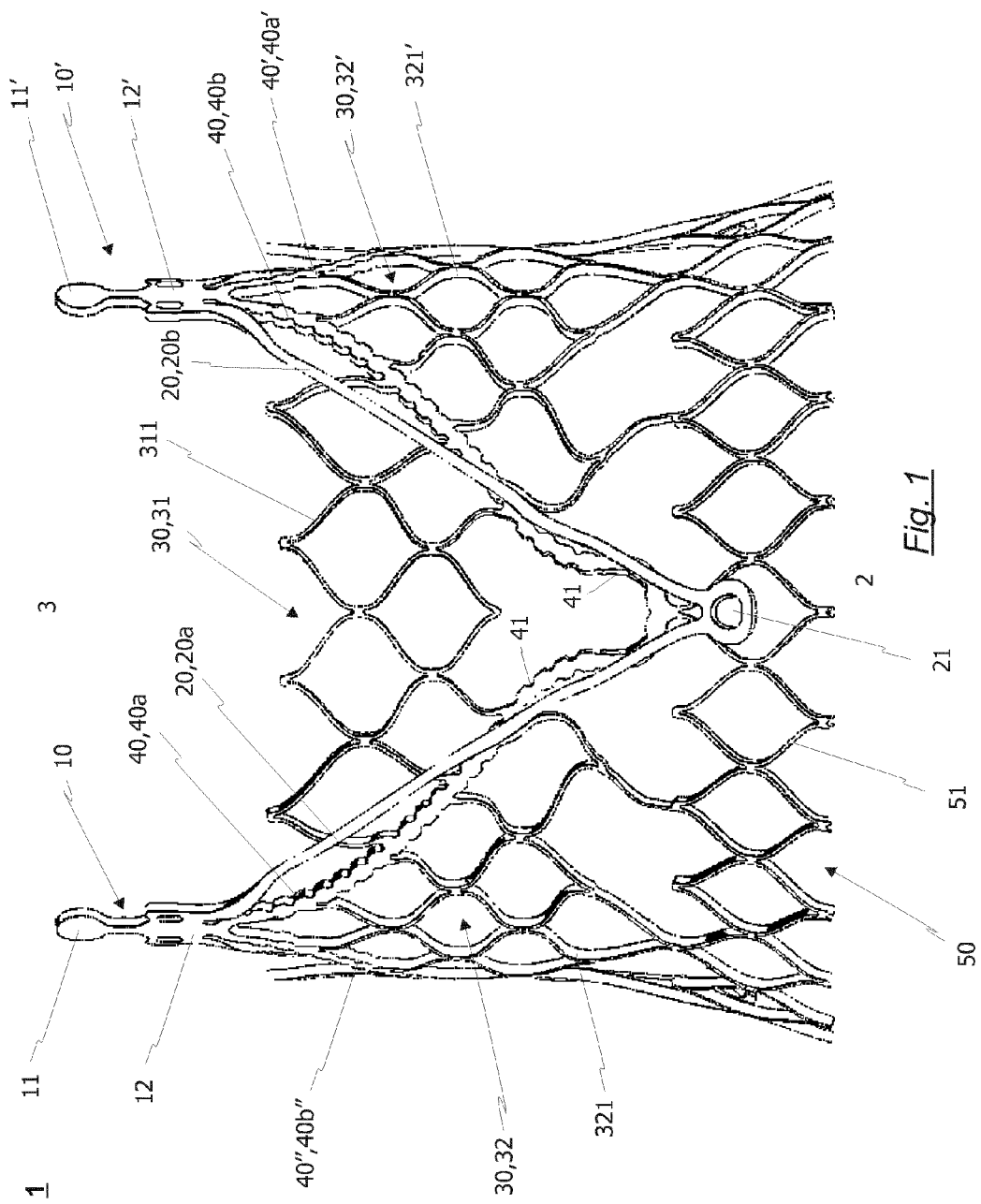

(52) U.S. Cl.
CPC ............... *A61F 2210/0019* (2013.01); *A61F 2220/0075* (2013.01); *A61F 2230/0054* (2013.01); *A61F 2230/0067* (2013.01); *A61F 2230/0069* (2013.01); *A61F 2250/0039* (2013.01)

(58) Field of Classification Search
USPC .................................................. 623/2.1–2.19
See application file for complete search history.

(56) References Cited

U.S. PATENT DOCUMENTS

| | | |
|---|---|---|
| 4,502,488 A | 3/1985 | Degironimo et al. |
| 4,922,905 A | 5/1990 | Strecker |
| 4,994,077 A | 2/1991 | Dobben |
| 5,002,566 A | 3/1991 | Carpentier et al. |
| 5,026,377 A | 6/1991 | Burton et al. |
| 5,035,706 A | 7/1991 | Giantureo et al. |
| 5,053,008 A | 10/1991 | Bajaj |
| 5,061,277 A | 10/1991 | Carpentier et al. |
| 5,094,661 A | 3/1992 | Levy et al. |
| 5,104,407 A | 4/1992 | Lam et al. |
| 5,163,953 A | 11/1992 | Vince |
| 5,197,979 A | 3/1993 | Quintero et al. |
| 5,211,183 A | 5/1993 | Wilson |
| 5,234,447 A | 8/1993 | Kaster et al. |
| 5,279,612 A | 1/1994 | Eberhardt |
| 5,332,402 A | 7/1994 | Teitelbaum |
| 5,336,258 A | 8/1994 | Quintero et al. |
| 5,350,399 A | 9/1994 | Erlebacher et al. |
| 5,352,240 A | 10/1994 | Ross |
| 5,368,608 A | 11/1994 | Levy et al. |
| 5,411,552 A | 5/1995 | Andersen et al. |
| 5,429,144 A | 7/1995 | Wilk |
| 5,456,713 A | 10/1995 | Chuter |
| 5,509,930 A | 4/1996 | Love |
| 5,540,712 A | 7/1996 | Kleshinski et al. |
| 5,549,666 A | 8/1996 | Hata et al. |
| 5,595,571 A | 1/1997 | Jaffe et al. |
| 5,609,626 A | 3/1997 | Quijano et al. |
| 5,613,982 A | 3/1997 | Goldstein |
| 5,632,778 A | 5/1997 | Goldstein |
| 5,643,278 A | 7/1997 | Wijay |
| 5,655,548 A | 8/1997 | Nelson et al. |
| 5,674,298 A | 10/1997 | Levy et al. |
| 5,679,112 A | 10/1997 | Levy et al. |
| 5,683,451 A | 11/1997 | Lenker et al. |
| 5,697,972 A | 12/1997 | Kim et al. |
| 5,713,953 A | 2/1998 | Vallana et al. |
| 5,733,325 A | 3/1998 | Robinson et al. |
| 5,746,775 A | 5/1998 | Levy et al. |
| 5,755,777 A | 5/1998 | Chuter |
| 5,817,113 A | 10/1998 | Gifford, III et al. |
| 5,824,041 A | 10/1998 | Lenker et al. |
| 5,824,080 A | 10/1998 | Lamuraglia |
| 5,840,081 A | 11/1998 | Andersen et al. |
| 5,841,382 A | 11/1998 | Walden et al. |
| 5,843,181 A | 12/1998 | Jaffe et al. |
| 5,855,601 A | 1/1999 | Bessler et al. |
| 5,876,434 A | 3/1999 | Flomenblit et al. |
| 5,880,242 A | 3/1999 | Hu et al. |
| 5,885,238 A | 3/1999 | Stevens et al. |
| 5,891,160 A | 4/1999 | Williamson, IV et al. |
| 5,899,936 A | 5/1999 | Goldstein |
| 5,928,281 A | 7/1999 | Huynh et al. |
| 5,935,163 A | 8/1999 | Gabbay |
| B151,044 I5 | 9/1999 | Lam et al. |
| 5,957,949 A | 9/1999 | Leonhardt et al. |
| 5,987,344 A | 11/1999 | West |
| 6,001,126 A | 12/1999 | Nguyen-Thien-Nhon |
| 5,061,277 B1 | 2/2000 | Carpentier et al. |
| 6,077,297 A | 6/2000 | Robinson et al. |
| 6,093,530 A | 7/2000 | McIlroy et al. |
| 6,102,944 A | 8/2000 | Huynh et al. |
| 6,117,169 A | 9/2000 | Moe |
| 6,126,685 A | 10/2000 | Lenker et al. |
| 6,168,614 B1 | 1/2001 | Andersen et al. |
| 6,177,514 B1 | 1/2001 | Pathak et al. |
| 6,183,481 B1 | 2/2001 | Lee et al. |
| 6,200,336 B1 | 3/2001 | Pavcnik et al. |
| 6,214,055 B1 | 4/2001 | Simionescu et al. |
| 6,231,602 B1 | 5/2001 | Carpentier et al. |
| 6,241,738 B1 | 6/2001 | Dereume |
| 6,254,564 B1 | 7/2001 | Wilk et al. |
| 6,254,636 B1 | 7/2001 | Peredo |
| 6,273,876 B1 | 8/2001 | Klima et al. |
| 6,283,995 B1 | 9/2001 | Moe et al. |
| 6,287,338 B1 | 9/2001 | Sarnowski et al. |
| 6,338,740 B1 | 1/2002 | Carpentier |
| 6,342,070 B1 | 1/2002 | Nguyen-Thien-Nhon |
| 6,344,044 B1 | 2/2002 | Fulkerson et al. |
| 6,350,278 B1 | 2/2002 | Lenker et al. |
| 6,352,547 B1 | 3/2002 | Brown et al. |
| 6,379,740 B1 | 4/2002 | Rinaldi et al. |
| 6,391,538 B1 | 5/2002 | Vyavahare et al. |
| 6,425,916 B1 | 7/2002 | Garrison et al. |
| 6,454,799 B1 | 9/2002 | Schreck |
| 6,471,723 B1 | 10/2002 | Ashworth et al. |
| 6,478,819 B2 | 11/2002 | Moe |
| 6,508,833 B2 | 1/2003 | Pavcnik et al. |
| 6,509,145 B1 | 1/2003 | Torrianni |
| 6,521,179 B1 | 2/2003 | Girardot et al. |
| 6,540,782 B1 | 4/2003 | Snyders |
| 6,558,417 B2 | 5/2003 | Peredo |
| 6,558,418 B2 | 5/2003 | Carpentier et al. |
| 6,572,642 B2 | 6/2003 | Rinaldi et al. |
| 6,582,462 B1 | 6/2003 | Andersen et al. |
| 6,585,766 B1 | 7/2003 | Huynh et al. |
| 6,613,086 B1 | 9/2003 | Moe et al. |
| 6,682,559 B2 | 1/2004 | Myers et al. |
| 6,730,118 B2 | 5/2004 | Spenser et al. |
| 6,736,845 B2 | 5/2004 | Marquez et al. |
| 6,767,362 B2 | 7/2004 | Schreck |
| 6,776,791 B1 | 8/2004 | Stallings et al. |
| 6,790,230 B2 | 9/2004 | Beyersdorf et al. |
| 6,808,529 B2 | 10/2004 | Fulkerson |
| 6,821,211 B2 | 11/2004 | Otten et al. |
| 6,821,297 B2 | 11/2004 | Snyders |
| 6,824,970 B2 | 11/2004 | Vyavahare et al. |
| 6,830,584 B1 | 12/2004 | Seguin |
| 6,861,211 B2 | 3/2005 | Levy et al. |
| 6,872,226 B2 | 3/2005 | Cali et al. |
| 6,881,199 B2 | 4/2005 | Wilk et al. |
| 6,893,460 B2 | 5/2005 | Spenser et al. |
| 6,908,481 B2 | 6/2005 | Cribier |
| 6,911,043 B2 | 6/2005 | Myers et al. |
| 6,945,997 B2 | 9/2005 | Huynh et al. |
| 6,974,474 B2 | 12/2005 | Pavcnik et al. |
| 7,014,655 B2 | 3/2006 | Barbarash et al. |
| 7,018,406 B2 | 3/2006 | Seguin et al. |
| 7,037,333 B2 | 5/2006 | Myers et al. |
| 7,050,276 B2 | 5/2006 | Nishiyama |
| 7,078,163 B2 | 7/2006 | Torrianni |
| 7,081,132 B2 | 7/2006 | Cook et al. |
| 7,101,396 B2 | 9/2006 | Artof et al. |
| 7,137,184 B2 | 11/2006 | Schreck et al. |
| 7,141,064 B2 | 11/2006 | Scott et al. |
| 7,163,556 B2 | 1/2007 | Xie et al. |
| 7,189,259 B2 | 3/2007 | Simionescu et al. |
| 7,198,646 B2 | 4/2007 | Figulla et al. |
| 7,201,772 B2 | 4/2007 | Schwammenthal et al. |
| 7,238,200 B2 | 7/2007 | Lee et al. |
| 7,252,682 B2 | 8/2007 | Seguin |
| 7,318,278 B2 | 1/2008 | Zhang et al. |
| 7,318,998 B2 | 1/2008 | Goldstein et al. |
| 7,322,932 B2 | 1/2008 | Xie et al. |
| 7,329,278 B2 | 2/2008 | Seguin et al. |
| 7,381,218 B2 | 6/2008 | Schreck |
| 7,393,360 B2 | 7/2008 | Spenser et al. |
| 7,399,315 B2 | 7/2008 | Iobbi |
| 7,452,371 B2 | 11/2008 | Pavcnik et al. |
| 7,473,275 B2 | 1/2009 | Marquez |
| 7,896,915 B2 | 3/2011 | Guyenot et al. |
| 7,914,575 B2 | 3/2011 | Guyenot et al. |

(56) References Cited

U.S. PATENT DOCUMENTS

| | | | |
|---|---|---|---|
| 8,398,704 B2* | 3/2013 | Straubinger | A61F 2/2418 623/1.15 |
| 8,465,540 B2* | 6/2013 | Straubinger | A61F 2/2418 623/1.24 |
| 8,790,395 B2* | 7/2014 | Straubinger | A61F 2/2418 623/1.15 |
| 9,439,759 B2* | 9/2016 | Straubinger | A61F 2/2418 |
| 2001/0011187 A1 | 8/2001 | Pavcnik et al. | |
| 2001/0021872 A1 | 9/2001 | Bailey et al. | |
| 2001/0039450 A1 | 11/2001 | Pavcnik et al. | |
| 2002/0010489 A1 | 1/2002 | Gayzel et al. | |
| 2002/0032481 A1 | 3/2002 | Gabbay | |
| 2002/0035390 A1 | 3/2002 | Schaldach et al. | |
| 2002/0045846 A1 | 4/2002 | Kaplon et al. | |
| 2002/0045929 A1 | 4/2002 | Diaz | |
| 2002/0055775 A1 | 5/2002 | Carpentier et al. | |
| 2002/0120322 A1 | 8/2002 | Thompson et al. | |
| 2002/0120323 A1 | 8/2002 | Thompson et al. | |
| 2002/0123790 A1 | 9/2002 | White et al. | |
| 2002/0133226 A1 | 9/2002 | Marquez et al. | |
| 2002/0143387 A1 | 10/2002 | Soetikno et al. | |
| 2002/0151970 A1 | 10/2002 | Garrison et al. | |
| 2002/0161426 A1 | 10/2002 | Iancea | |
| 2002/0177840 A1 | 11/2002 | Farnholtz | |
| 2002/0198594 A1 | 12/2002 | Schreck | |
| 2003/0027332 A1 | 2/2003 | Lafrance et al. | |
| 2003/0036791 A1 | 2/2003 | Philipp et al. | |
| 2003/0036795 A1 | 2/2003 | Andersen et al. | |
| 2003/0040792 A1 | 2/2003 | Gabbay | |
| 2003/0050694 A1 | 3/2003 | Yang et al. | |
| 2003/0055495 A1 | 3/2003 | Pease et al. | |
| 2003/0065386 A1 | 4/2003 | Weadock | |
| 2003/0114913 A1 | 6/2003 | Spenser et al. | |
| 2003/0125795 A1 | 7/2003 | Pavcnik et al. | |
| 2003/0139796 A1 | 7/2003 | Sequin et al. | |
| 2003/0139803 A1 | 7/2003 | Sequin et al. | |
| 2003/0149476 A1 | 8/2003 | Damm et al. | |
| 2003/0153974 A1 | 8/2003 | Spenser et al. | |
| 2003/0195620 A1 | 10/2003 | Huynh et al. | |
| 2003/0236570 A1 | 12/2003 | Cook et al. | |
| 2004/0006380 A1 | 1/2004 | Buck et al. | |
| 2004/0039436 A1 | 2/2004 | Spenser et al. | |
| 2004/0049262 A1 | 3/2004 | Obermiller et al. | |
| 2004/0073289 A1 | 4/2004 | Hartley et al. | |
| 2004/0078950 A1 | 4/2004 | Schreck et al. | |
| 2004/0093060 A1 | 5/2004 | Seguin et al. | |
| 2004/0093063 A1 | 5/2004 | Wright et al. | |
| 2004/0117004 A1 | 6/2004 | Osborne et al. | |
| 2004/0117009 A1 | 6/2004 | Cali et al. | |
| 2004/0148018 A1 | 7/2004 | Carpentier et al. | |
| 2004/0153145 A1 | 8/2004 | Simionescu et al. | |
| 2004/0186558 A1 | 9/2004 | Pavcnik et al. | |
| 2004/0186563 A1 | 9/2004 | Lobbi | |
| 2004/0186565 A1 | 9/2004 | Schreck | |
| 2004/0193244 A1 | 9/2004 | Hartley et al. | |
| 2004/0206363 A1 | 10/2004 | McCarthy et al. | |
| 2004/0210301 A1 | 10/2004 | Obermiller et al. | |
| 2004/0210304 A1 | 10/2004 | Seguin et al. | |
| 2004/0210306 A1 | 10/2004 | Quijano et al. | |
| 2004/0243143 A1 | 12/2004 | Corcoran et al. | |
| 2004/0249343 A1 | 12/2004 | Cioanta | |
| 2004/0260389 A1 | 12/2004 | Case et al. | |
| 2005/0009000 A1 | 1/2005 | Wilhelm et al. | |
| 2005/0033220 A1 | 2/2005 | Wilk et al. | |
| 2005/0033398 A1 | 2/2005 | Seguin | |
| 2005/0043790 A1 | 2/2005 | Seguin | |
| 2005/0049692 A1 | 3/2005 | Numamoto et al. | |
| 2005/0060018 A1 | 3/2005 | Dittman | |
| 2005/0075725 A1 | 4/2005 | Rowe | |
| 2005/0075776 A1 | 4/2005 | Cho | |
| 2005/0096726 A1 | 5/2005 | Sequin et al. | |
| 2005/0096736 A1 | 5/2005 | Osse et al. | |
| 2005/0098547 A1 | 5/2005 | Cali et al. | |
| 2005/0113902 A1 | 5/2005 | Geiser et al. | |
| 2005/0113910 A1 | 5/2005 | Paniagua et al. | |
| 2005/0119728 A1 | 6/2005 | Sarac | |
| 2005/0119736 A1 | 6/2005 | Zilla et al. | |
| 2005/0125075 A1 | 6/2005 | Meade et al. | |
| 2005/0137499 A1 | 6/2005 | Sheets et al. | |
| 2005/0137609 A1 | 6/2005 | Guiraudon | |
| 2005/0137682 A1 | 6/2005 | Justino | |
| 2005/0137687 A1 | 6/2005 | Salahieh et al. | |
| 2005/0137688 A1 | 6/2005 | Salahieh et al. | |
| 2005/0137690 A1 | 6/2005 | Salahieh et al. | |
| 2005/0137697 A1 | 6/2005 | Salahieh et al. | |
| 2005/0137698 A1 | 6/2005 | Salahieh et al. | |
| 2005/0137702 A1 | 6/2005 | Haug et al. | |
| 2005/0143804 A1 | 6/2005 | Haverkost | |
| 2005/0143807 A1 | 6/2005 | Pavcnik et al. | |
| 2005/0149166 A1 | 7/2005 | Schaeffer et al. | |
| 2005/0150775 A1 | 7/2005 | Zhang et al. | |
| 2005/0171597 A1 | 8/2005 | Boatman et al. | |
| 2005/0171598 A1 | 8/2005 | Schaeffer | |
| 2005/0192665 A1 | 9/2005 | Spenser et al. | |
| 2005/0197695 A1 | 9/2005 | Stacchino et al. | |
| 2005/0222668 A1 | 10/2005 | Schaeffer et al. | |
| 2005/0234546 A1 | 10/2005 | Nugent et al. | |
| 2005/0267560 A1 | 12/2005 | Bates | |
| 2006/0009842 A1 | 1/2006 | Huynh et al. | |
| 2006/0025857 A1 | 2/2006 | Bergheim et al. | |
| 2006/0047343 A1 | 3/2006 | Oviatt et al. | |
| 2006/0058864 A1 | 3/2006 | Schaeffer et al. | |
| 2006/0074484 A1 | 4/2006 | Huber | |
| 2006/0111770 A1 | 5/2006 | Pavcnik et al. | |
| 2006/0136034 A1 | 6/2006 | Modesitt et al. | |
| 2006/0142846 A1 | 6/2006 | Pavcnik et al. | |
| 2006/0149360 A1 | 7/2006 | Schwammenthal et al. | |
| 2006/0155366 A1 | 7/2006 | LaDuca et al. | |
| 2006/0167543 A1 | 7/2006 | Bailey et al. | |
| 2006/0193885 A1 | 8/2006 | Neethling et al. | |
| 2006/0210597 A1 | 9/2006 | Hiles | |
| 2006/0224183 A1 | 10/2006 | Freudenthal | |
| 2006/0229561 A1 | 10/2006 | Huszar | |
| 2006/0229718 A1 | 10/2006 | Marquez | |
| 2006/0229719 A1 | 10/2006 | Marquez et al. | |
| 2006/0246584 A1 | 11/2006 | Covelli | |
| 2006/0259134 A1 | 11/2006 | Schwammenthal et al. | |
| 2006/0259136 A1 | 11/2006 | Nguyen et al. | |
| 2006/0259137 A1 | 11/2006 | Artof et al. | |
| 2006/0265056 A1 | 11/2006 | Nguyen et al. | |
| 2006/0287717 A1 | 12/2006 | Rowe et al. | |
| 2006/0287719 A1 | 12/2006 | Rowe et al. | |
| 2006/0290027 A1 | 12/2006 | O'Connor et al. | |
| 2006/0293745 A1 | 12/2006 | Carpentier et al. | |
| 2007/0005129 A1 | 1/2007 | Damm et al. | |
| 2007/0005131 A1 | 1/2007 | Taylor | |
| 2007/0005132 A1 | 1/2007 | Simionescu et al. | |
| 2007/0020248 A1 | 1/2007 | Everaerts et al. | |
| 2007/0021826 A1 | 1/2007 | Case et al. | |
| 2007/0027535 A1 | 2/2007 | Purdy, Jr. et al. | |
| 2007/0038291 A1 | 2/2007 | Case et al. | |
| 2007/0038295 A1 | 2/2007 | Case et al. | |
| 2007/0043435 A1 | 2/2007 | Seguin et al. | |
| 2007/0050014 A1 | 3/2007 | Johnson | |
| 2007/0056346 A1 | 3/2007 | Spenser et al. | |
| 2007/0088431 A1 | 4/2007 | Bourang et al. | |
| 2007/0093887 A1 | 4/2007 | Case et al. | |
| 2007/0100435 A1 | 5/2007 | Case et al. | |
| 2007/0100440 A1 | 5/2007 | Figulla et al. | |
| 2007/0112422 A1 | 5/2007 | Dehdashtian | |
| 2007/0123700 A1 | 5/2007 | Ueda et al. | |
| 2007/0123979 A1 | 5/2007 | Perier et al. | |
| 2007/0142906 A1 | 6/2007 | Figulla et al. | |
| 2007/0162103 A1 | 7/2007 | Case et al. | |
| 2007/0173932 A1 | 7/2007 | Cali et al. | |
| 2007/0179592 A1 | 8/2007 | Schaeffer | |
| 2007/0185565 A1 | 8/2007 | Schwammenthal et al. | |
| 2007/0203576 A1 | 8/2007 | Lee et al. | |
| 2007/0213813 A1 | 9/2007 | Von Segesser et al. | |
| 2007/0239271 A1 | 10/2007 | Nguyen | |
| 2007/0244551 A1 | 10/2007 | Stobie | |
| 2007/0260327 A1 | 11/2007 | Case et al. | |
| 2007/0288087 A1 | 12/2007 | Fearnot et al. | |
| 2008/0004688 A1 | 1/2008 | Spenser et al. | |

(56) References Cited

U.S. PATENT DOCUMENTS

| | | |
|---|---|---|
| 2008/0021546 A1 | 1/2008 | Patz et al. |
| 2008/0022504 A1 | 1/2008 | Melsheimer |
| 2008/0033534 A1 | 2/2008 | Cook et al. |
| 2008/0065011 A1 | 3/2008 | Marchand et al. |
| 2008/0071361 A1 | 3/2008 | Tuval et al. |
| 2008/0071362 A1 | 3/2008 | Tuval et al. |
| 2008/0071363 A1 | 3/2008 | Tuval et al. |
| 2008/0071366 A1 | 3/2008 | Tuval et al. |
| 2008/0071368 A1 | 3/2008 | Tuval et al. |
| 2008/0071369 A1 | 3/2008 | Tuval et al. |
| 2008/0077236 A1 | 3/2008 | Letac et al. |
| 2008/0086205 A1 | 4/2008 | Gordy et al. |
| 2008/0097586 A1 | 4/2008 | Pavcnik et al. |
| 2008/0102439 A1 | 5/2008 | Tian et al. |
| 2008/0127707 A1 | 6/2008 | Kokish et al. |
| 2008/0133003 A1 | 6/2008 | Seguin et al. |
| 2008/0140189 A1 | 6/2008 | Nguyen et al. |
| 2008/0147182 A1 | 6/2008 | Righini et al. |
| 2008/0154355 A1 | 6/2008 | Benichou et al. |
| 2008/0200977 A1 | 8/2008 | Paul et al. |
| 2008/0215143 A1 | 9/2008 | Seguin |
| 2008/0221703 A1 | 9/2008 | Que et al. |
| 2008/0255660 A1 | 10/2008 | Guyenot et al. |
| 2008/0255661 A1 | 10/2008 | Straubinger et al. |
| 2008/0262602 A1 | 10/2008 | Wilk et al. |
| 2008/0269878 A1 | 10/2008 | Iobbi |
| 2008/0275549 A1 | 11/2008 | Rowe |
| 2009/0093876 A1 | 4/2009 | Nitzan et al. |
| 2009/0216312 A1 | 8/2009 | Straubinger et al. |
| 2009/0222076 A1 | 9/2009 | Figulla et al. |
| 2010/0100167 A1 | 4/2010 | Bortlein et al. |
| 2010/0160725 A1 | 6/2010 | Kiser et al. |
| 2010/0249915 A1 | 9/2010 | Zhang |
| 2010/0249916 A1 | 9/2010 | Zhang |
| 2010/0249917 A1 | 9/2010 | Zhang |
| 2010/0249918 A1 | 9/2010 | Zhang |
| 2010/0262231 A1 | 10/2010 | Tuval et al. |
| 2011/0093007 A1 | 4/2011 | Abbott et al. |
| 2011/0208290 A1 | 8/2011 | Straubinger et al. |
| 2011/0208297 A1 | 8/2011 | Tuval et al. |
| 2011/0295363 A1* | 12/2011 | Girard ............... A61F 2/2412 623/1.26 |
| 2011/0319989 A1 | 12/2011 | Lane et al. |
| 2016/0158003 A1* | 6/2016 | Wallace ............ A61F 2/2409 623/2.17 |
| 2016/0166384 A1* | 6/2016 | Olson ................ A61F 2/07 623/2.17 |
| 2017/0049563 A1* | 2/2017 | Straubinger ........ A61F 2/07 |
| 2017/0065410 A1* | 3/2017 | Straubinger ........ A61F 2/07 |

FOREIGN PATENT DOCUMENTS

| | | |
|---|---|---|
| CA | 2436258 A1 | 1/2005 |
| CA | 2595233 A1 | 7/2006 |
| CA | 2627555 | 5/2007 |
| CN | 1745727 A | 3/2006 |
| CN | 2762776 Y | 3/2006 |
| CN | 1897892 A | 1/2007 |
| CN | 2933337 Y | 8/2007 |
| CN | 101431963 A | 5/2009 |
| CN | 101605509 A | 12/2009 |
| CN | 101623217 A | 1/2010 |
| CN | 101700199 A | 5/2010 |
| CN | 101720211 A | 6/2010 |
| CN | 102271626 A | 12/2011 |
| DE | 4316971 A1 | 11/1994 |
| DE | 19532846 A1 | 3/1997 |
| DE | 19546692 A1 | 6/1997 |
| DE | 19633901 A1 | 2/1998 |
| DE | 20003874 U1 | 6/2000 |
| DE | 19857887 A1 | 7/2000 |
| DE | 10010073 A1 | 9/2001 |
| DE | 10010074 A1 | 10/2001 |
| DE | 10034105 C1 | 4/2002 |
| DE | 101 21 210 A1 | 11/2002 |
| DE | 19546692 C2 | 11/2002 |
| DE | 10301026 A1 | 2/2004 |
| DE | 10302447 A1 | 7/2004 |
| DE | 10335948 B3 | 2/2005 |
| DE | 10010074 B4 | 4/2005 |
| DE | 19857887 B4 | 5/2005 |
| DE | 10010073 B4 | 12/2005 |
| DE | 10 2005 051 849 | 5/2007 |
| DE | 10 2005 052628 A1 | 5/2007 |
| DE | 20 2007 005 491 U1 | 7/2007 |
| DE | 20221871 U1 | 10/2008 |
| EP | 0084395 A1 | 7/1983 |
| EP | 0402036 B1 | 12/1990 |
| EP | 0402176 B1 | 12/1990 |
| EP | 0411118 A1 | 2/1991 |
| EP | 0458877 B1 | 4/1991 |
| EP | 0515324 A1 | 11/1992 |
| EP | 0547135 B1 | 6/1993 |
| EP | 0657147 A2 | 6/1995 |
| EP | 0 592 410 B1 | 10/1995 |
| EP | 0 592 410 B1 | 11/1995 |
| EP | 0729364 B1 | 9/1996 |
| EP | 0756498 B1 | 5/1997 |
| EP | 0778775 B1 | 6/1997 |
| EP | 0826346 A1 | 3/1998 |
| EP | 0896813 A2 | 2/1999 |
| EP | 0903122 A2 | 3/1999 |
| EP | 0928615 A1 | 7/1999 |
| EP | 0938877 A2 | 9/1999 |
| EP | 0986348 B1 | 3/2000 |
| EP | 1 251 805 B1 | 10/2000 |
| EP | 1041942 B1 | 10/2000 |
| EP | 1041943 B1 | 10/2000 |
| EP | 1117446 B1 | 7/2001 |
| EP | 1 233 731 B1 | 5/2002 |
| EP | 1206179 B1 | 5/2002 |
| EP | 1251804 B1 | 10/2002 |
| EP | 0 971 649 B1 | 12/2002 |
| EP | 1281357 A2 | 2/2003 |
| EP | 1281375 A2 | 2/2003 |
| EP | 1 017 868 B1 | 9/2003 |
| EP | 1354569 A1 | 10/2003 |
| EP | 1452153 A1 | 9/2004 |
| EP | 0987998 B1 | 10/2004 |
| EP | 1 087 727 B1 | 11/2004 |
| EP | 1499366 B1 | 1/2005 |
| EP | 1518518 A2 | 3/2005 |
| EP | 1 253 875 B1 | 4/2005 |
| EP | 1 251 803 B1 | 6/2005 |
| EP | 1469797 B1 | 11/2005 |
| EP | 1 690 515 A1 | 8/2006 |
| EP | 1 255 510 B1 | 3/2007 |
| EP | 1112042 B1 | 11/2007 |
| EP | 1878407 A1 | 1/2008 |
| EP | 1886649 A2 | 2/2008 |
| EP | 1 900 343 A2 | 3/2008 |
| EP | 1259195 B1 | 10/2008 |
| EP | 1980220 A1 | 10/2008 |
| EP | 1994913 A2 | 11/2008 |
| EP | 2 000 115 A2 | 12/2008 |
| EP | 2474287 A1 | 7/2012 |
| FR | 2788217 A1 | 7/2000 |
| FR | 2815844 A1 | 5/2002 |
| FR | 2828263 A1 | 2/2003 |
| GB | 2433700 A | 7/2007 |
| GB | 2440809 A | 2/2008 |
| JP | 52-86296 | 7/1977 |
| JP | 62-227352 | 10/1987 |
| JP | 1049571 A | 2/1989 |
| JP | 7-504091 | 5/1995 |
| JP | 2001-526574 | 12/2001 |
| JP | 2004-504111 A | 2/2002 |
| JP | 2002-525168 A | 8/2002 |
| JP | 2002-525169 A | 8/2002 |
| JP | 2002-536115 A | 10/2002 |
| JP | 2003-515386 A | 5/2003 |
| JP | 2003-523262 | 8/2003 |
| JP | 2003-524504 | 8/2003 |

(56) References Cited

FOREIGN PATENT DOCUMENTS

| | | |
|---|---|---|
| JP | 2004-283461 A | 10/2004 |
| JP | 2005-118585 | 5/2005 |
| JP | 2007-521125 A | 8/2007 |
| JP | 2007-296375 | 11/2007 |
| JP | 2008-539985 A | 11/2008 |
| JP | 2009-131397 A | 6/2009 |
| JP | 2009-534157 A | 9/2009 |
| JP | 2010-526609 A | 8/2010 |
| WO | WO 92/12690 | 8/1982 |
| WO | WO-90/09102 | 8/1990 |
| WO | WO 91/17720 A1 | 11/1991 |
| WO | WO 95/11055 A1 | 4/1995 |
| WO | WO-95/24873 | 9/1995 |
| WO | WO-95/28183 | 10/1995 |
| WO | WO 95/29713 A1 | 11/1995 |
| WO | WO-96/13227 | 5/1996 |
| WO | WO 97/27893 A1 | 8/1997 |
| WO | WO 97/27898 A1 | 8/1997 |
| WO | WO-97/32615 | 9/1997 |
| WO | WO 98/08456 A1 | 3/1998 |
| WO | WO 98/11846 A1 | 3/1998 |
| WO | WO 98/19633 A1 | 5/1998 |
| WO | WO 98/43556 | 10/1998 |
| WO | WO-98/46165 | 10/1998 |
| WO | WO 98/53761 A1 | 12/1998 |
| WO | WO 99/36001 A1 | 7/1999 |
| WO | WO-99/37337 | 7/1999 |
| WO | WO 99/42058 A1 | 8/1999 |
| WO | WO 99/53987 A1 | 10/1999 |
| WO | WO-99/66863 | 12/1999 |
| WO | WO 00/02503 A1 | 1/2000 |
| WO | WO 00/15148 | 3/2000 |
| WO | WO 00/18330 | 4/2000 |
| WO | WO 00/18333 A1 | 4/2000 |
| WO | WO-00/18445 | 4/2000 |
| WO | WO 00/21464 A1 | 4/2000 |
| WO | WO 2000/25702 A1 | 5/2000 |
| WO | WO 00/47139 A1 | 8/2000 |
| WO | WO-00/53125 | 9/2000 |
| WO | WO-00/62714 | 10/2000 |
| WO | WO 00/69367 A1 | 11/2000 |
| WO | WO 00/78226 A1 | 12/2000 |
| WO | WO-01/10209 A1 | 2/2001 |
| WO | WO 2001/35870 A1 | 5/2001 |
| WO | WO-01/41679 A1 | 6/2001 |
| WO | WO 2001/039700 A1 | 6/2001 |
| WO | WO 01/49213 A2 | 7/2001 |
| WO | WO-01/51104 A1 | 7/2001 |
| WO | WO 01/54625 A1 | 8/2001 |
| WO | WO-01/58503 A1 | 8/2001 |
| WO | WO 01/62189 A1 | 8/2001 |
| WO | WO 01/64137 A1 | 9/2001 |
| WO | WO 02/22054 A1 | 3/2002 |
| WO | WO 2002/36048 A1 | 5/2002 |
| WO | WO-02/058745 A1 | 8/2002 |
| WO | WO-02/100301 A1 | 12/2002 |
| WO | WO-02/102286 A1 | 12/2002 |
| WO | WO 03/003949 A2 | 1/2003 |
| WO | WO-03/007795 A2 | 1/2003 |
| WO | WO 2003/003949 A2 | 1/2003 |
| WO | WO-03/009785 A1 | 2/2003 |
| WO | WO 03/013239 | 2/2003 |
| WO | WO 2003/011195 A2 | 2/2003 |
| WO | WO 03/028592 A1 | 4/2003 |
| WO | WO 03/047468 A1 | 6/2003 |
| WO | WO 03/051231 A2 | 6/2003 |
| WO | WO-03/079928 A2 | 10/2003 |
| WO | WO 03/079933 A1 | 10/2003 |
| WO | WO 03/092554 A1 | 11/2003 |
| WO | WO 2003/096935 A1 | 11/2003 |
| WO | WO 2004/004597 A2 | 1/2004 |
| WO | WO 2004/016200 A1 | 2/2004 |
| WO | WO 2004/016201 A2 | 2/2004 |
| WO | WO 2004/019825 A1 | 3/2004 |
| WO | WO-2004/026117 A2 | 4/2004 |
| WO | WO 2004/026173 A2 | 4/2004 |
| WO | WO 2004/028399 A2 | 4/2004 |
| WO | WO 2004/030515 A2 | 4/2004 |
| WO | WO 2004/043301 A1 | 5/2004 |
| WO | WO 2004/064671 A2 | 8/2004 |
| WO | WO 2004/082527 A2 | 9/2004 |
| WO | WO 2004/082528 A2 | 9/2004 |
| WO | WO 2004/096100 A1 | 11/2004 |
| WO | WO 2005/011534 A1 | 2/2005 |
| WO | WO 2005/021063 A2 | 3/2005 |
| WO | WO 2005/034812 A1 | 4/2005 |
| WO | WO 2005/062980 A2 | 7/2005 |
| WO | WO 2005/063980 A1 | 7/2005 |
| WO | WO 2005/070343 A1 | 8/2005 |
| WO | WO-2005/072654 A1 | 8/2005 |
| WO | WO 2005/102015 A2 | 11/2005 |
| WO | WO 2006/066327 | 6/2006 |
| WO | WO-2006/066327 A1 | 6/2006 |
| WO | WO 2006/070372 A2 | 7/2006 |
| WO | WO 2006/076890 | 7/2006 |
| WO | WO 2006/089517 A1 | 8/2006 |
| WO | WO-2006/102063 A2 | 9/2006 |
| WO | WO 2006/108090 A2 | 10/2006 |
| WO | WO-2006/124649 A2 | 11/2006 |
| WO | WO 2006/124649 A2 | 11/2006 |
| WO | WO 2006/127756 A2 | 11/2006 |
| WO | WO 2006/127765 A1 | 11/2006 |
| WO | WO 2006/129441 A1 | 12/2006 |
| WO | WO-2006/132948 A1 | 12/2006 |
| WO | WO 2006/133959 A1 | 12/2006 |
| WO | WO 2007/047488 A2 | 4/2007 |
| WO | WO 2007/047945 A2 | 4/2007 |
| WO | WO 2007/048529 A1 | 5/2007 |
| WO | WO-2007/048529 A1 | 5/2007 |
| WO | WO 2007/051620 A1 | 5/2007 |
| WO | WO 2007/059252 A1 | 5/2007 |
| WO | WO-2007/071436 A2 | 6/2007 |
| WO | WO 2007/098232 A2 | 8/2007 |
| WO | WO 2007/120543 A1 | 10/2007 |
| WO | WO 2007/123956 | 11/2007 |
| WO | WO-2008/028569 A1 | 3/2008 |
| WO | WO 2008/031103 A2 | 3/2008 |
| WO | WO 2008/035337 A2 | 3/2008 |
| WO | WO 2008/045949 | 4/2008 |
| WO | WO 2008/051554 A2 | 5/2008 |
| WO | WO 2008/070797 A2 | 6/2008 |
| WO | WO 2008/079962 A1 | 7/2008 |
| WO | WO 2008/098191 A2 | 8/2008 |
| WO | WO 2008/101083 A2 | 8/2008 |
| WO | WO 2008/125153 A1 | 10/2008 |
| WO | WO 2008/138584 A1 | 11/2008 |
| WO | WO 2008/150529 A1 | 12/2008 |
| WO | WO 2009/053497 A1 | 4/2009 |
| WO | WO 2009/094188 A2 | 7/2009 |
| WO | WO 2009/106545 A1 | 9/2009 |
| WO | WO 2009/149462 A2 | 12/2009 |
| WO | WO 2011/008812 A2 | 1/2011 |
| WO | WO 2011/060386 A1 | 5/2011 |
| WO | WO 2011/104269 A1 | 9/2011 |
| WO | WO 2011/120050 A1 | 9/2011 |
| WO | WO 2011/144351 A2 | 11/2011 |
| WO | WO 2011/147849 A1 | 12/2011 |
| WO | WO 2012/023980 A1 | 2/2012 |
| WO | WO 2012/036742 A2 | 3/2012 |
| WO | WO 2012/038550 A1 | 3/2012 |
| WO | WO 2012/039748 A2 | 3/2012 |
| WO | WO 2012/082952 A2 | 6/2012 |
| WO | WO 2012/106491 A1 | 8/2012 |
| WO | WO 2012/142189 A1 | 10/2012 |

OTHER PUBLICATIONS

Aortenklappenbioprothese erfolgreich in der Entwicklung, May 16, 2003 (1 page).
English translation of Aortenklappenbioprothese erfolgreich in der Entwicklung (2 pages).
Screen shots from http://www.fraunhofer.de/presse/filme/2006/index.jsp, 2006 (2 pages).

(56) References Cited

OTHER PUBLICATIONS

Liang, Ma, et al., "Double-crowned valved stents for off-pump mitral valve replacement," *Eur. J. Cardio-Thoracic Surgery*, vol. 28, pp. 194-198 (2005) (5 pages).

Huber, Christoph H., et al. "Direct Access Valve Replacement (DAVR)—are we entering a new era in cardiac surgery?" *Eur. J. Cardio-Thoracic Surgery*, vol. 29, pp. 380-385 (2006) (6 pages).

File history for German Patent DE 195 46 692 filed Dec. 14, 1995 and patented Jul. 11, 2002 (111 pages).

Klein, Allan L. et al., "Age-related Prevalence of Valvular Regurgitation in Normal Subjects: A Comprehensive Color Flow Examination of 118 Volunteers," *J. Am. Soc. Echocardiography*, vol. 3, No. 1, pp. 54-63 (1990) (10 pages).

Gummert, J.F. et al., "Cardiac Surgery in Germany During 2007: A Report on Behalf of the German Society for Thoracic and Cardiovascular Surgery," *Thorac. Cardiov. Surg.*, vol. 56, pp. 328-336 (2008) (9 pages).

Gummert, J.F. et al., "Cardiac Surgery in Germany During 2006: A Report on Behalf of the German Society for Thoracic and Cardiovascular Surgery," *Thorac. Cardiov. Surg.*, vol. 55, pp. 343-350 (2007) (8 pages).

Ferrari, M.W. et al., "Transarterial Aortic Valve Replacement with a Self expanding Stent in Pigs," *Heart*, vol. 90, No. 11, pp. 1326-1331 (2004).

Ferrari, "Entwicklung eines Verfahrens zum transvaskulären Aortenklappenersatz," Habilitationsschrift, Medizinische Fakultät der Friedrich-Schiller-Universität Jena, pp. 49-52, dated Sep. 2003.

Ferrari, "Entwicklung eines Verfahrens zum transvaskulären Aortenklappenersatz," Habilitationsschrift, Medizinische Fakultät der Friedrich-Schiller-Universität Jena, pp. 1-159, dated Sep. 2003.

German National Library, bibliographic information for Ferrari, M., "Entwicklung eines Verfahrens zum transvaskulären Aortenklappenersatz," available at https://www.deutsche-digitale-bibliothek.de/item/U2RQV45RMES4YP6AHEPGN4QPJWAMGROI.

\* cited by examiner

RADIALLY COLLAPSIBLE FRAME FOR A PROSTHETIC VALVE AND METHOD FOR MANUFACTURING SUCH A FRAME

This application is a U.S. national stage filing under 35 U.S.C. § 371 of International Application No. PCT/EP2014/065817, filed on Jul. 23, 2014, incorporated by reference herein in its entirety, which claims the benefit of priority to European Patent Application No. 13182346.0, filed on Aug. 30, 2013.

The present invention relates to a radially collapsible frame for a prosthetic heart valve and a method for manufacturing such a frame. Specifically, the present invention relates to a radially collapsible frame for a prosthetic valve used in the treatment of a stenosis (narrowing) of a cardiac valve and/or a cardiac valve insufficiency. In addition, the present invention relates to an endoprosthesis comprising the inventive radially collapsible frame.

The expression "narrowing (stenosis) of a cardiac valve and/or cardiac valve insufficiency" is intended to include a functional defect of one or more cardiac valves which is either genetic or has developed. A cardiac defect of this type might affect each of the four heart valves, although the valves in the left ventricle (aortic and mitral valves) are affected much more often than the right sided part of the heart (pulmonary and tricuspid valves). The functional defect can result in narrowing (stenosis), inability to close (insufficiency) or a combination of the two (combined vitium).

Radially collapsible frames for prosthetic heart valves are known in the state of the art. In particular, minimally-invasive forms of treatment of cardiac valves have been developed recently which are characterized by allowing the procedure to be performed under local anesthesia. One approach provides for the use of a catheter system to implant a self-expandable frame, which is connected to a collapsible valvular prosthesis. Such a self-expandable endoprosthesis can be guided via a catheter system to the implantation site within the heart through an inguinal artery or vein. After reaching the implantation site, the radially collapsible frame can be unfolded so as to anchor the endoprosthesis in the vicinity of a native valve annulus.

To this end, it is known that the radially collapsible frame may be comprised of, for example, a plurality of self-expanding substantially longitudinal arches, the arches being configured to hold a valvular prosthesis in place at the desired implantation site. The prior art document EP 1 980 220 A1, for instance, discloses a self-expandable stent having three retaining arms (20) which form the base for an anchoring segment for accommodating a valvular prosthesis (40). In order to automatically position and orientate the common frame described by the EP 1 980 220 A1, a total of three positioning arches (10) are provided. The positioning arches (10) have a rounded head portion (12) which engages the pockets of an insufficient heart valve, which shall be replaced by the known endoprosthesis. These three positioning arches (10) ensure that the requisite positioning accuracy can be obtained in the direction of rotation and provide for additional radial clamping forces in order to support the implantation of the stent at the desired implantation side.

Additionally, when the known frame (1) is in its expanded state, the respective positioning arms of the positioning arches (10) are located in the pockets of the diseased heart valve and thus essentially guarantee secure and error-free positioning of the medical device. The pocket flaps of the diseased heart valve are then clamped between the positioning arches (10) and the retaining arches (20), in a manner similar to a paper-clip, due to the expansion of the endoprosthesis 1. This further assists in achieving an optimum positioning and anchoring of the known heart valve frame.

As a consequence of the clamping effect between the positioning arches (10) and the retaining arches (20), the radially collapsible frames known from the prior art tend to allow for a frictional contact between the valvular prosthesis and the diseased native heart valves, as the valvular prosthesis is frequently directly connected to the retaining arches of the collapsible frame. Such a frictional contact between the diseased heart valve and the valvular prosthesis can result in increased wear of the valvular prosthesis, due to undesired friction with the diseased heart valve. Furthermore, due to the common frame configuration, the diseased heart valve may impede the motion of the valvular prosthesis, especially during the opening movement of the prosthetic valve leaflet. In some circumstances, this may mean that the prosthetic heart valve leaflets may not be able to open fully, as a consequence of the presence of the diseased heart valve leaflets. Moreover, the common stent structures often fail to provide for sufficient radial forces in order to anchor the stent structure at the desired implantation side. As a consequence, inadvertent relocation of the stent after implantation may occur.

On the basis of the problems outlined above, certain embodiments of the present invention address the issue of providing a radially collapsible frame for a prosthetic valve, which guarantees perfect positioning of the heart valve prosthesis and, at the same time, protects the prosthetic valvular leaflets effectively from external stresses due to a frictional contact with the native heart valve leaflets. In addition, the inventive frame should provide for a treatment of the narrowed cardiac valve or cardiac valve insufficiency by way of a simple and reliable procedure to enable a routine treatment without major stress to the patient.

In this regard, and as it will be described in more detail below, the invention provides a radially collapsible frame for a prosthetic heart valve comprising an outflow region at a proximal end of the frame and an inflow end region at a distal end of the frame, opposite to the outflow end region. The radially collapsible frame further includes at least two radially spaced commissure attachment regions located at the outflow end of the frame and being configured to receive commissures of the prosthetic valve leaflets. A cell structure composed of a plurality of lattice cells is being arranged radially around a flow axis of the frame and connects the at least two commissure attachment regions. Finally, the radially collapsible frame further comprises at least one anchoring/positioning arch, wherein said at least one anchoring/positioning arch radially overlaps the cell structure, at least partially.

In medical terms, the commissure of a heart valve is a point or line of union or junction between the respective leaflets of a heart valve. In the closed state of a heart valve, the commissures can be described as the points or lines of a leaflet, contacting another leaflet in order to close the particular blood vessel. Naturally, the leaflets of a heart valve are continuously in contact with each other at two or more commissure edges which are radially distributed about the flow axis of a prosthetic heart valve. In this connection, the expression "commissure attachment region" describes an arrangement of struts located at the outflow end of the inventive stent, which is configured to receive the at least two commissure edges of the leaflets. Normally, the number of commissure attachment regions complies with the number of commissure edges formed by the leaflets.

Furthermore, the term "radially overlapping" expresses that the at least one anchoring/positioning arch is located along the same section of the frames flow axis as the cell structure. The anchoring/or positioning arch is, however, not part of the cell structure but radially distanced therefrom. In particular, the at least one anchoring/positioning arch may extend radially outwardly from the circumference of the cell structure, and hence, overlap the latter at least partly.

Accordingly, the inventive frame has the advantage that a cell structure, which is composed of a plurality of lattice cells, prevents any undesired contact between the native heart valve leaflets and the valvular prosthesis. In particular, the cell structure is disposed between the valvular prosthesis and the leaflets of the native valve. Therefore, the cell structure forms a separation wall in between and, additionally, provides for an improved clamping effect of the native heart valve leaflets together with the at least one anchoring/positioning arch. Moreover, the inventive collapsible frame does not necessarily have to provide for retaining arches, as it is conceivable to attach the valvular prosthesis directly to the plurality of lattice cells of the cell structure, by means of threads for example. Finally, it should be noted that the cell structure provides for an additional support of the inventive frame at the desired implantation side.

According to another embodiment of the present invention, the at least one anchoring/positioning arch of the collapsible frame may be rigidly attached to the at least two radially spaced commissure attachment regions. In particular, it is preferred to form the at least anchoring/positioning arch integrally with the at least two radially spaced commissure attachment regions as a single piece. In this way, the inventive radially collapsible frame is particularly robust and provides for a stable support of the valvular prosthesis within a patient's blood vessel. As it will be described in more detail below, all of the parts of the inventive frame may be cut out of a single hollow tube of shape memory material. Consequently, the radially overlapping at least one anchoring/positioning arch does not need to be fixed to the collapsible frame, by means of sutures, welding or adhesive, after the radially spaced commissure attachment regions and the cell structure have been cut out of the hollow metal tube. Instead, the at least one anchoring/positioning arch is cut out of the same hollow tube as the rest of the radially collapsible frame, wherein the at least one anchoring/positioning arch is formed proximally of the outflow end region of the frame and bend in a distal direction (towards the inflow end), so as to radially overlap the cell structure, after a laser cutting has been performed.

Of course, it is also feasible to apply other means of attaching the anchoring/positioning arch rigidly to the frame, such as welding, sewing, gluing or riveting for instance. According to this alternative, the at least one anchoring/positioning arch is formed as separate piece and attached to the frame structure subsequently, after the frame has been cut out of the hollow metal tube. In more detail, the at least one separate anchoring/positioning arch may be welded to the commissure attachment regions in such a way that the at least one anchoring/positioning arch radially overlaps the cell structure at least partially and extends in a direction towards the in flow end of the frame. As a consequence, it is not necessary to bend the at least one anchoring/position arch during a shape-setting process of the frame.

In accordance with another aspect of the present invention, the inventive frame further comprises a plurality of circumferentially arranged retaining arches, each including first and second arms joined to one another at a distal end of the retaining arches. The two arms of each respective retaining arch are joined by a rounded structure. The provision of circumferentially arranged retaining arches provides for various advantages effects. In particular, the retaining arches, which substantially range from the outflow end to the inflow end of the inventive frame, protrude radially in the expanded state of the frame to press against the wall of a patient's blood vessel in which the frame is deployed with a radially-acting contact force. The shape of the retaining arches may be configured to be positioned below the native valve annulus or to be positioned at least on the native valve annulus, thereby providing additional anchoring for the inventive stent together with a valvular prosthesis affixed thereto. As an alternative or in addition to the cell structure of the frame, the retaining arches may be used in order to attach the valvular prosthesis to the collapsible frame. In particular, a cusp edge of the valvular prosthesis may be sutured to the retaining arches, at an opposite and of the free commissure edges of the leaflets. In this connection, the first and second arms of each retaining arch may be shaped in such a way as to imitate the natural arcuate shape of the cusp edges of a native heart valve.

To this end, the two arms of each retaining arch are joined to one another at a connection, preferably having a substantially U- or V-shaped structure. As mentioned before, this particular shape of the retaining arches may particularly imitate the natural shape of a heart valve cusp region. The U- or V-shaped retaining arches may be located in such a way that the closed portion of the U- or V-shape forms the connection of the two arms in a distal direction, towards the inflow end of the frame. The open ends of the U- or V-shaped structure, on the contrary, may be attached to the at least two commissure attachment regions. Therefore, the retaining arches preferably have an open end directed towards the outflow end of the radially collapsible frame.

According to another embodiment, an entirety of three anchoring/positioning arches and an entirety of three retaining arches are provided at the inventive frame. Consequently, it is preferable to further provide for an entirety of three radially spaced commissure attachment regions, which are connected to the three anchoring/positioning arches and the three retaining arches respectively. In this regard, each first arm of the three anchoring/positioning arches or retaining arches respectively may be connected with a first commissure attachment region, whereas each second arm may be attached to a second neighboring commissure attachment region. In this way, each anchoring position arch and each retaining arch is connected with at least two of the radially spaced commissure attachments of the frame. The provision of three retaining arches is particularly useful when accommodating a valvular prosthesis having three flexible leaflets such as an aortic valve, for example. The same applies to the number of anchoring/positioning arches, which should comply with the number of leaflets of the valvular prosthesis so as to guarantee a suitable orientation of each leaflet at the desired implantation site.

As already indicated, the adjacent arms of two neighboring retaining arches preferably merge at one of the commissure attachment regions, near the outflow end region of the frame. Accordingly, each of the retaining arches is connected to a neighboring retaining arch at one of the commissure attachment regions, forming a circumferentially aligned attachment region for the cusp edges of the valvular prosthesis.

In another embodiment, the cell structure of the frame comprises a first cell region composed of a plurality of first cells, the first cells being arranged between the respective first and second arms of each retaining arch. Additionally, the cell structure may comprise a second cell region composed of a plurality of second cells, the second cells being arranged between adjacent arms of two neighboring retaining arches. In other words, the cell structure is preferably composed of at least two different cell types, which are arranged in an alternating manner radially around a flow axis of the frame. The first and second cell regions are intersected by the respective arms of the retaining arches. Preferably, the first and second cells of the first and second cell regions are constructed with a similar pattern and size. However, it is also conceivable to construct the first and second cells with differently. In particular, it may be desirable to implement a denser cell structure in the second cell region compared to the density of the cell structure in the first cell region. This is because the mainly second cell region provides for the stability of the inventive frame, whereas the first cell region is mainly provided in order to protect the valvular prosthesis from any direct contact with the native heart valves. Of course, however, the first cell region being arranged between the respective first and second arms of each retaining arch, also adds to the stability of the present frame.

In a particularly preferred embodiment, the at least one anchoring/positioning arch particularly radially overlaps the first cell region of the cell structure. In other words, the at least one anchoring/positioning arch is preferably arranged in between the respective first and second arms of each retaining arch, and thus, circumferentially aligned with the retaining arches.

According to another embodiment, each of the first cells or second cells is formed by a plurality of struts. Accordingly, each of the struts is either connected with one of the neighboring cells of the respective cell regions or with one of the arms of the retaining arches respectively. As already indicated above, each of the struts of the first and second cells is preferably formed by a laser cutting of a hollow shaped memory metal tube, providing for integrally connected first and second cells of the frame structure.

As already indicated above, each of the positioning arches and each of the retaining arches include a closed end directed towards the inflow end of the frame, wherein the closed end of a respective anchoring/positioning arch is substantially circumferentially aligned with respect to the closed end of an associated retaining arch. In other words, the positioning arches are configured symmetrically to the retaining arches although preferably disposed somewhat further towards the outflow region of the frame. Moreover, the upper end of the positioning arches may be connected to the upper ends of the associated retaining arches by means of the at least two radially space commissure attachment regions in the outflow region of the frame. In the expanded state of the frame, both, the commissure attachment region and the respective upper end of the positioning and retaining arches spread out so that a radially-acting force is exerted on a blood vessel wall, thereby enabling secure anchoring of the stent at the site of implantation. The circumferentially aligned lower end of the anchoring/positioning arch, on the other hand, spreads out even further than the retaining arches and the cell structure, so as to be able to engage the pockets of the native heart valve, thereby clamping the native heart valve leaflets between the lower of the anchoring/position arch and the lower end of the respective retaining arch.

In another embodiment, the present radially collapsible frame comprises at least one fastening portion by means of which a valvular prosthesis is connected to the frame. The at least one fastening portion preferably extends along the longitudinal axis of the frame and comprises a plurality of fastening holes distributed in a longitudinal direction at a discrete position along the length of the at least one fastening portion. A thread of thin wire may be guided through each fastening hole to secure the valvular prosthesis to the stent. The advantage of this feature is that longitudinal displacement of the valvular relative to the frame is a substantially minimized once implanted and so the prosthesis is not unduly disturbed or weakened as a result of the hearts peristaltic motion.

In addition to fastening holes, the fastening portion may include one or more notches to assist the seating and retaining of suture material. The notches also assist with an even attachment of the prosthesis to the frame and similarly to the fastening holes, minimizing longitudinal displacement of the prosthesis. The fastening portions are preferably formed as an integral part of the retaining arches. Nevertheless, it is also conceivable to implement fastening portions along any of the remaining structures of the inventive frame, such as the commissure attachment regions.

According to another embodiment, the retaining arches have a shape that matches the leaflets of a prosthetic valve attached to the frame, in the expanding state of the frame. This specific design of the respective arms of the retaining arches is unique for catheter delivered valves as it provides for heart valve durability advantages. The so formed arms of the retaining arches for supporting the cusp edge of the leaflets of the valvular prosthesis are attached to the frame across a gap behind the positioning arches and the cell structure respectively.

In order to further increase the support of the frame at the implantation site, the inventive frame may comprise at least one annular collar which is connected to a part of the rounded structure at a distal end section of the respective arms of the retaining arches. That is, the lower end section of each arm of the retaining arches may merge into an annular collar, which provides an additional anchoring measure for the frame. Furthermore, the annular collar may also be connected to the lower end of the second cell region. The annular collar may exhibit a plurality of supporting webs which run parallel to the longitudinal axis of the fame in its collapsed state and are inter-connected by transversal webs. In the expanded state of the frame, however, the supporting webs and the transversal webs of the annular collar may form a rhomboid or serpentine-like annular collar which abuts against the vascular wall of the patient. Therefore, the annular collar serves a supporting body through which the radial forces developing due to the self-expansion are transmitted to the vascular wall. Since a relatively large contact area of the frame interacts with the vascular wall, because of the structure of the annular collar, there may be a decreased risk of injury to artery or the tissue despite the increased radial forces. Moreover, the annular collar may be used to attach a skirt portion of the valvular prosthesis to the inventive frame. In this way, the risk for paravalvular leakage can be substantially reduced.

Each of the supporting webs of the annular collar may further provide for an eyelet as an additional fastening means. In this regard, the eyelets are uniformly distributed around the inflow end section of the frame, thereby providing a more uniform fixation of a valvular prosthesis to the frame. Hence, the risk of an actual displacement of the valvular prosthesis relative to the frame may be reduced.

According to another aspect of the present invention, the lower end section of the annular collar constitute at least one flared or tapered section, in the expanded state of the frame, thereby providing for an improved fixation for the frame in the position of the native cardiac valve and for preventing antegrade migration of the frame having a valvular prosthesis affixed thereto.

Preferably, the annular collar has a flared or tapered section with a radial shape. However, it is also conceivable that the flared or tapered section is not uniform along the circumference of the frame. For example, the annular collar may have a flare only near the location of the positioning arches, wherein no flares are provided near the commissure attachment regions, i.e. the regions in between the two arms of two neighboring position arches.

According to a most advantages embodiment, the annular collar may comprise a flared and a tapered section at the same time. In particular, the upper end of the annular collar, which is connected to the lower end of the retaining arches and to the lower end of the second cell region respectively, may be flared, whereas the lower end of the annular collar, which is located at the inflow end of the frame, may be tapered. In simple terms, the annular collar may have a substantially pear-shaped configuration, which effectively prevents damage to the patient's heart vessel caused by contact with the annular collar. If the present frame is used in order to support the implantation of a prosthetic aortic heart valve, for example, this specific configuration of the annular collar is particularly advantageous. This is because the pear-shaped annular collar prevents the frame from irritating the heart conduction system by stimulating the bundle of his which is located below the natural heart valve annulus, i.e. at the position where the annular collar is supposed to be arranged. By forming the annular collar in a pear-shape, it is possible to exclusively contact the lower region of the native heart valve annulus so as to support the inventive frame at the implantation site. Any region further into the heart chamber, on the other hand, is not affected by the annular collar, as the lower end section is tapered and hence does not contact the walls of the heart chamber at whole.

In another embodiment, the inventive frame has a scalloped inflow edge designed at its distal end when the frame is in its expanded state. Hence, the inflow edge of the frame does not lie entirely in the plane perpendicular to the longitudinal direction of the frame. Rather, the edge of the frame at its inflow end region may have a scalloped shape. In addition, the scalloped inflow edge may also be flared or tapered around its circumference or only at the selected location. For example, one embodiment may include a flare at the inflow edge only near the location of the positioning arches and transition to a none-flared straight cylindrical shape in the area between two neighboring positioning arches. In particular, the location of the respective flares and the respective straight cylindrical shape may be determined by the location of the arms of the respective retaining arches to which the tissue component (s) of the valvular prosthesis is attached. The scalloped shape generally follows the native valve annulus and does not compromise the ability of the valve to seal against leakage.

As will be described in more detail below, when manufacturing the inventive frame, it is conceivable for the frame to exhibit a structure integrally cut from a portion of a hollow tube, in particular from a small metal tube, which incorporates all of the structures of the frame at the same time. Specifically, it is conceivable to use a laser beam to cut the stent structure from the small metal tube.

The small metal tube is most preferably a shape memory material such that the frame exhibits an integrally-formed structure which can transform from a first pre-definable shape into a second pre-definable shape. Therefore, the frame exhibits a first pre-definable shape (collapsed shape) during insertion into the patient's body and a second pre-definable shape (expanded shape) once it is implanted. Because of the frames design, during the transition of the frame from the first pre-definable shape into the second pre-definable shape, the positioning arches and the cell structure radially expand as a function of the cross-sectional expansion of the frame. The frames second shape is preferably selected such that when the frame is expanded, the cell structure abuts against the wall of the blood vessel in which the frame is deployed. In addition, the lower ends of the cell structure which are positioned beneath the native valve annulus, provide additional anchoring of the stent.

When the frame consists of shaped memory material, the material is preferably being designed such that the frame can transform from a temporary shape into a permanent shape under the influence of an external stimulus. In this regard, the temporary shape is the frames first shape (i.e. the collapsed state of the frame) while the permanent shape is assumed in the frames second shape (i.e. in the second state of the frame). In particular, the use of a shape memory material such as Nitinol, i.e. an equiatomic alloy of nickel and titanium, allows for a particularly gentle implantation procedure when implanting the frame. When manufacturing the frame from a shape memory material, the frame structure is preferably shaped after it has been cut into a stent pattern from a hollow tube. As will be described in more detail below, once the desired shape has been formed by bending the structures of the frame, this shape is "fixed". This process is known as "programming". Programming may be affected by heating the frame structure, forming the frame into the desired shape and then cooling the frame. Programming may also be affected by forming and shaping the frame structure at low temperatures, this being known as "cold stretching". The permanent shape is thus saved, enabling the frame to be stored and implanted in a temporary, non-formed shape. If an external stimulus then acts on the stents structure, the shape memory effect is activated and the saved permanent shape is restored.

A particularly preferred embodiment provides for the external stimulus to be a definable switching temperature. It is thus conceivable that the stent material needs to be heated to a higher temperature than the switching temperature in order to activate the shape memory effect and thus regenerate the saved permanent shape of the stent. A specific switching temperature can be preset by the relevant selection of the chemical composition of the shape memory material and the heating time during programming.

It is particularly preferred to set the switching temperature to be in the range of between room temperature and the patient's body temperature. Doing so is of advantage, especially with regard to the medical device being used as an implant in a patient's body. Accordingly, all that needs to be ensured when implanting the frame is that the frame is warmed up to the patient's body temperature (37° C.) at the site of implementation so as to activate the shape memory effect of the frame material.

By means of the inventive frame, a diseased native heart valve may be treated. In this connection a prosthetic valve (valvular prosthesis) is supported on the inventive radially collapsible frame. Thereafter, the at least one anchoring/positioning arch is positioned within a pocket of the native heart valve. Subsequently, at least a portion of the native heart valve is positioned between the at least one anchoring/positioning arch and the plurality of cells of the cell structure. Finally, a radial force is applied against a portion of the vascular wall, by means of the commissure attachment region and the cell structure, for example, so as to fix the frame and the prosthetic valve to the desired implantation site.

As already indicated before, the present invention further relates to an endoprosthesis comprising the inventive radially collapsible frame. The endoprosthesis further includes a valvular prosthesis which is attached to an inner surface of the frame, preferably by means of sutures. The endoprosthesis may be used to treat any deficient heart valve, most preferably a deficient aortic heart valve. Due to the inventive structure of the radially collapsible frame, the endoprosthesis can be fixed securely to the native heart valve annulus and exhibits a particularly high wear resistance.

For the majority of patients undergoing treatment, it is preferable for the endoprosthesis to have an outer diameter of approximately 7.0 mm to approximately 5.0 mm in its first shape so that the valvular prosthesis can be introduced with a 23F delivery system (given an external diameter of 7.0 mm) or with a 17F delivery system (given an external diameter of 5.0 mm).

Due to the new frame design, the inventive endoprosthesis can achieve an outer diameter between approximately 4.0 mm to approximately 8.0 mm in its first shape. Accordingly, the new endoprosthesis may be introduced with a 20F delivery system, preferably an 18F delivery system, more preferably a 16F delivery system and most preferably a 14F delivery system. Therefore, the endoprosthesis according to the present invention can be introduced into a patient's blood vessel easier and causes less damage.

After the endoprosthesis has been released from the catheter tip, in the implanted state respectively, the endoprosthesis exhibits a second predefined shape in which the stent and the valve assembly affixed thereto is in an expanded state (expanded condition). Depending on the patient being treated, it is preferable for the frame to exhibit a diameter of between 19.0 mm and 27.0 mm in its second shape and implanted state.

The present invention further relates to a method for manufacturing a radially collapsible frame according to the present invention. In particular, the inventive method comprises a step for providing a hollow tube made of shaped memory material, followed by a step for scanning a beam of laser radiation over a desired region of the hollow tube, such that a desired pattern is cut into the tube, thereby cutting a stent pattern. In particular, the laser scanning step is configured in such a way that the stent pattern comprises a basic frame cell structure defining a mash, composed of a plurality of cells, each cell being formed by a plurality of struts, and at least one anchoring/positioning arch extending away from the plurality of cells of the cell structure. In other words, by scanning the hollow tube with a beam of laser radiation, a stent pattern is cut out comprising a cell structure and at least one anchoring/positioning arch located above the latter cell structure.

Subsequently, in a shape setting process, the final structure of the radially collapsible frame is defined by bending the at least one anchoring/positioning arch into the direction of the cell structure in such a way that the at least one anchoring/positioning arch extends in substantially the same direction as the plurality of cells of the cell structure. Accordingly, the so bent at least one anchoring/positioning arch radially overlaps the plurality of cells of the cells structure at least partially. As a consequence, the at least one anchoring/positioning arch is radially distanced from the cell structure of the frame. That is, the at least one anchoring/positioning arch is positioned in a radial distance from a flow axis of the frame, which is further than the cell structure.

In order to prevent the beam of laser radiation from cutting two opposite ends of the hollow tube made of shaped memory material at the same time, the step for scanning the metal tube with a beam of laser radiation may include a step for placing the hollow tube on a mandrel. Thus, after cutting one surface of the hollow tube, the beam of laser radiation hits the surface of the mandrel and hence does not affect another opposite part of the hollow tube. In this connection, it should be noted that the cut out stent pattern is removed from the mandrel before the aforementioned shape-setting process of the inventive method is performed.

According to another embodiment of the present method, the shape setting process may apply a heat treatment process to the stent pattern. In more detail, the heat treatment process can be used in order to set the permanent shape of the frame to a shape with an at least partly radially overlapping anchoring/positioning arch. Of course, the permanent shape is configured to be the expanded shape of the inventive collapsible frame. That is, in the temporary shape the frame is flexible and hence can be collapsed in order to be introduced by an insertion device.

The following will make reference to the included drawings and describe preferred embodiments of the frame according to the present invention in greater detail.

Figure 2:
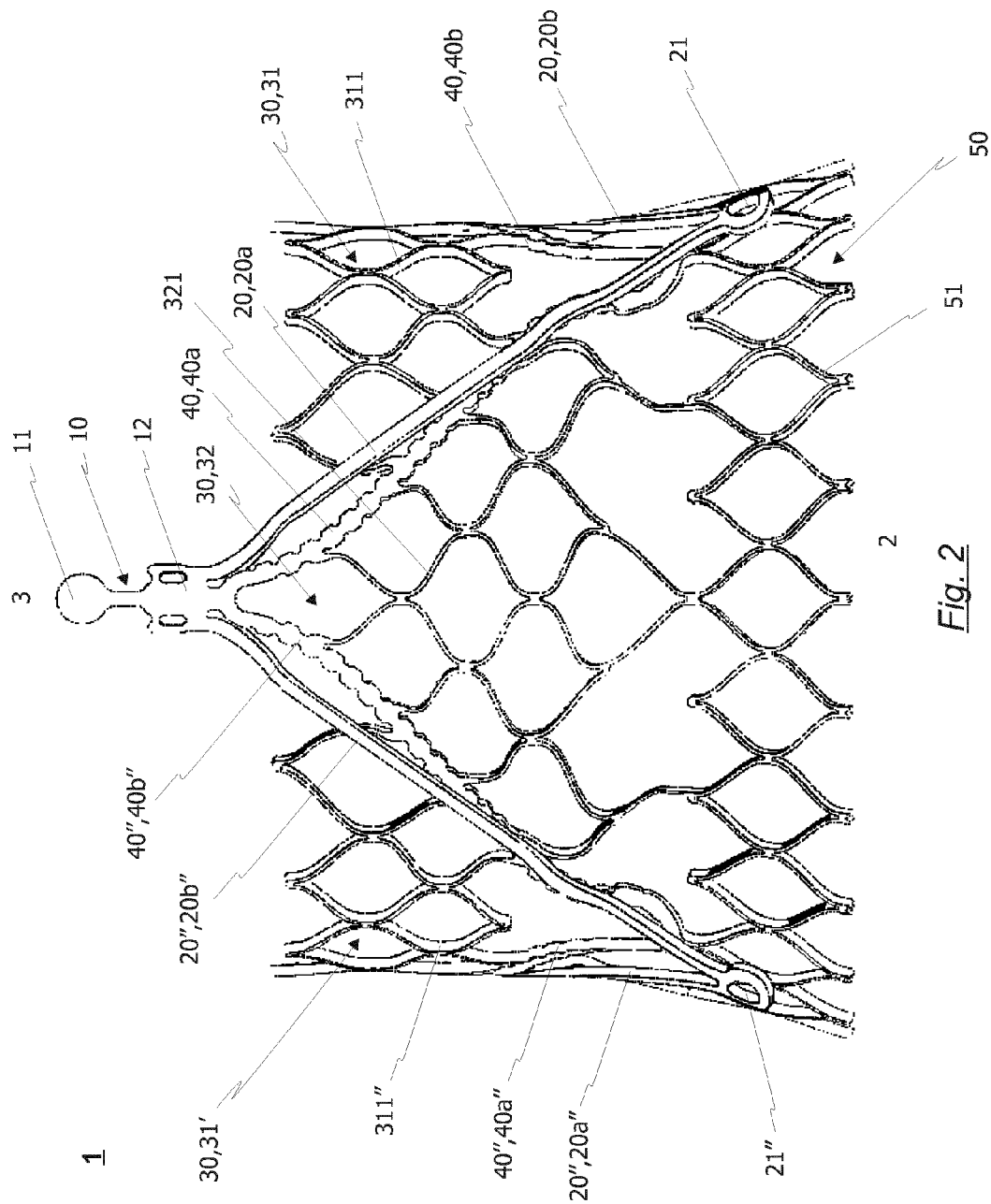
Figure 3:
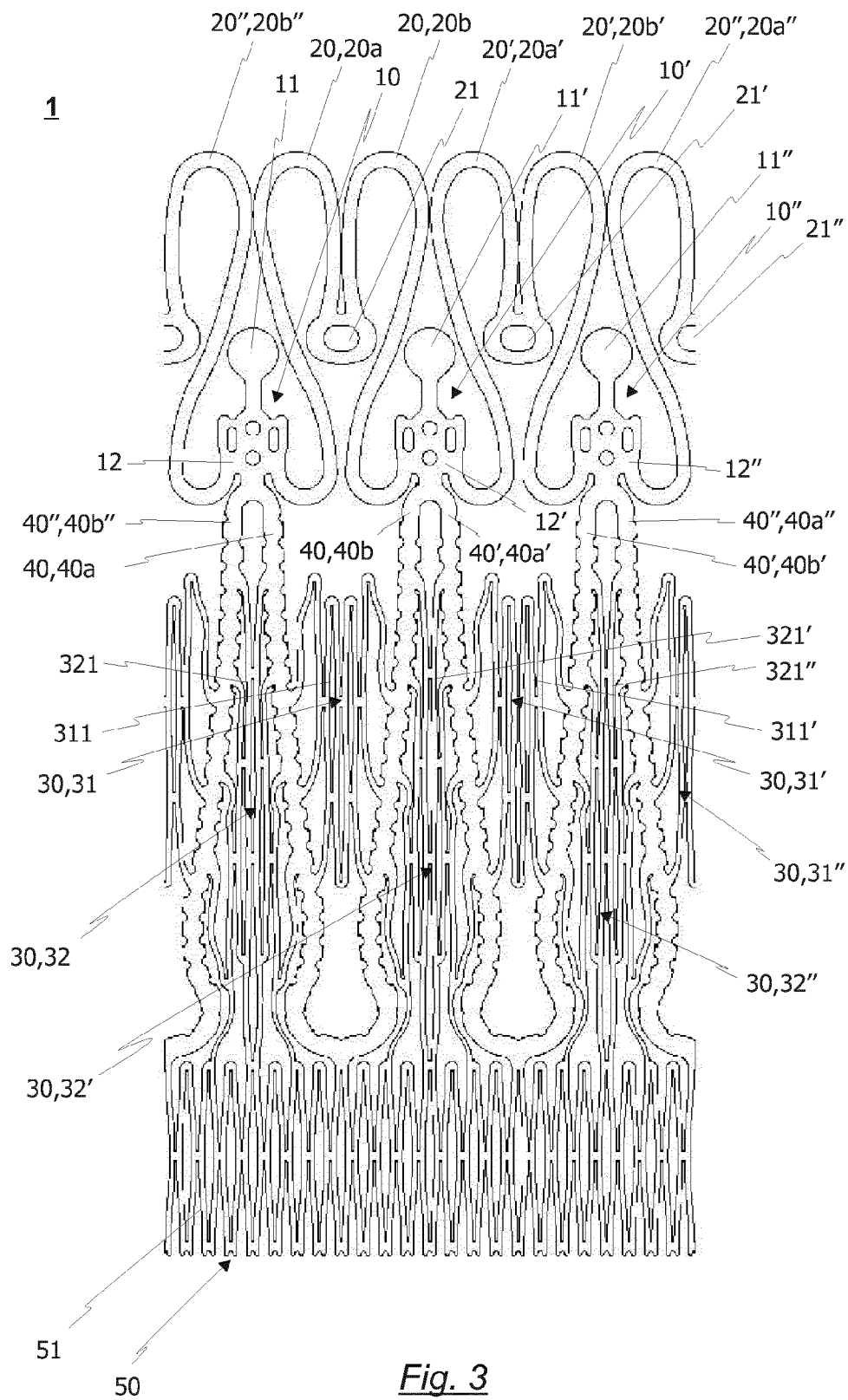

Shown are:

FIG. 1 a perspective side view of a first embodiment of the radially collapsible frame according to the present invention, capable of supporting and anchoring a valvular prosthesis, shown in its expanded state;

FIG. 2 a second perspective side view of the frame according to the first embodiment shown in FIG. 1; and FIG. 3 a flat roll-out view of a preferred embodiment of the cut out stent pattern, which can be used to manufacture a radially collapsible frame in accordance with the present invention.

Figure 4A:
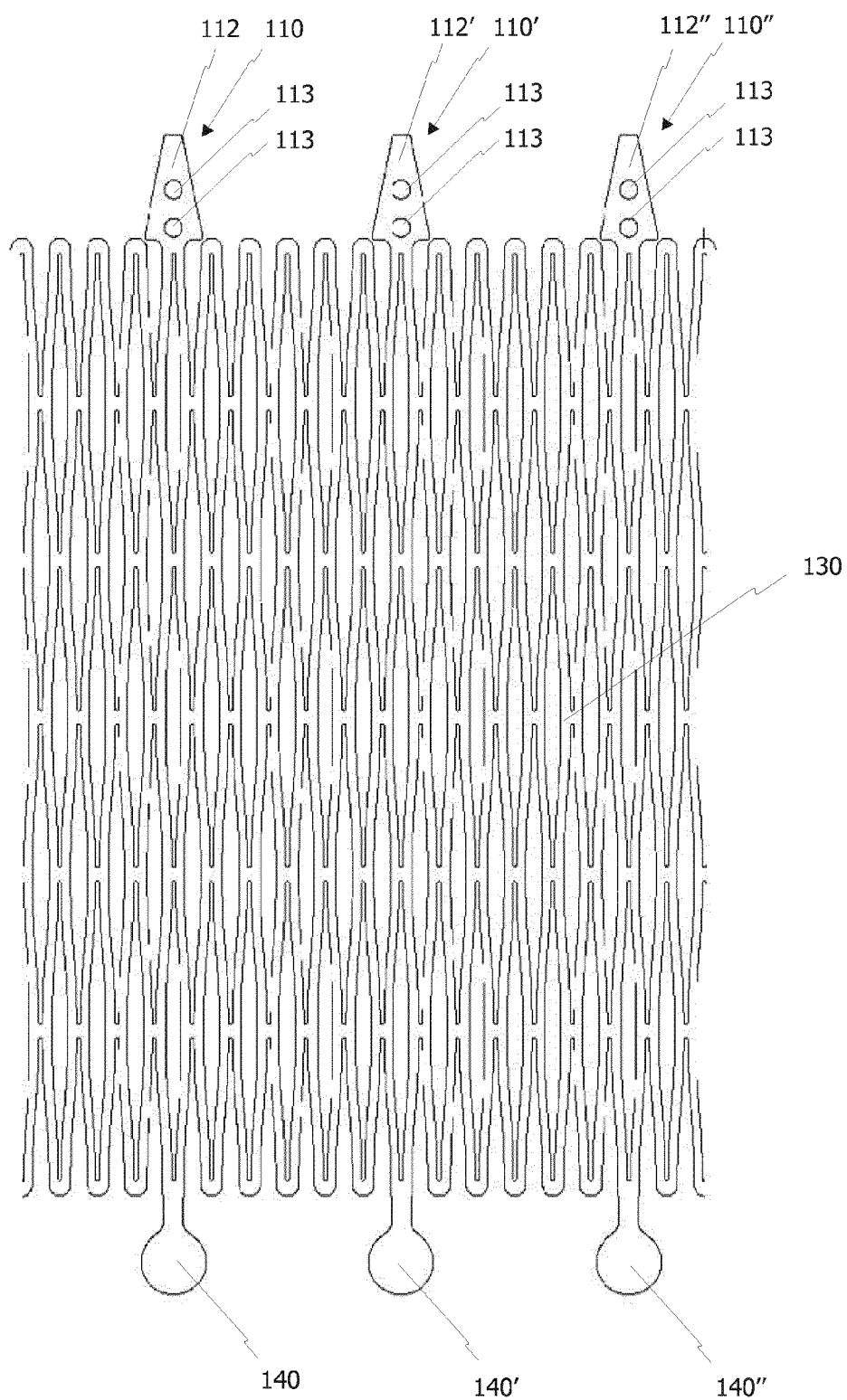
Figure 4B:
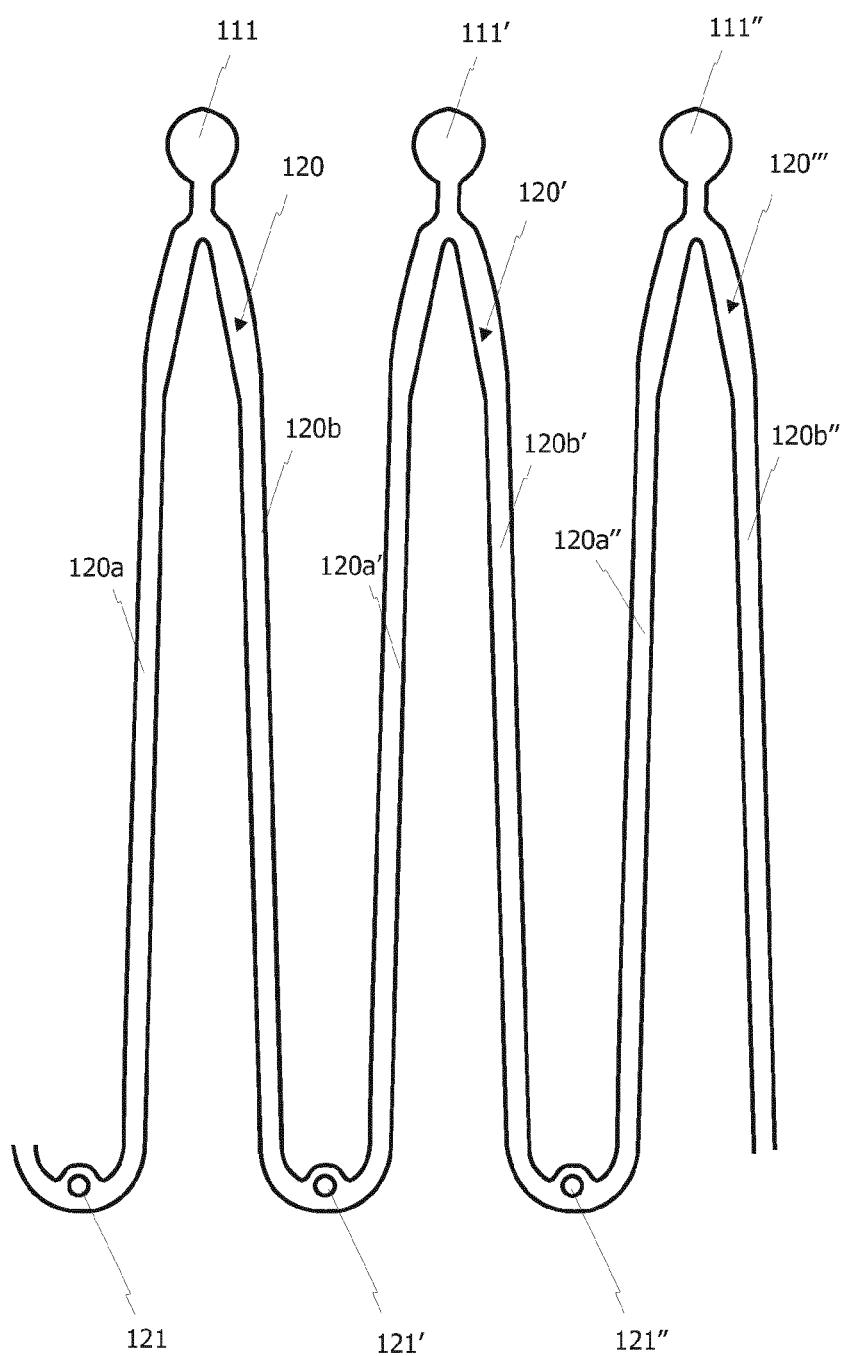
Figure 4C:
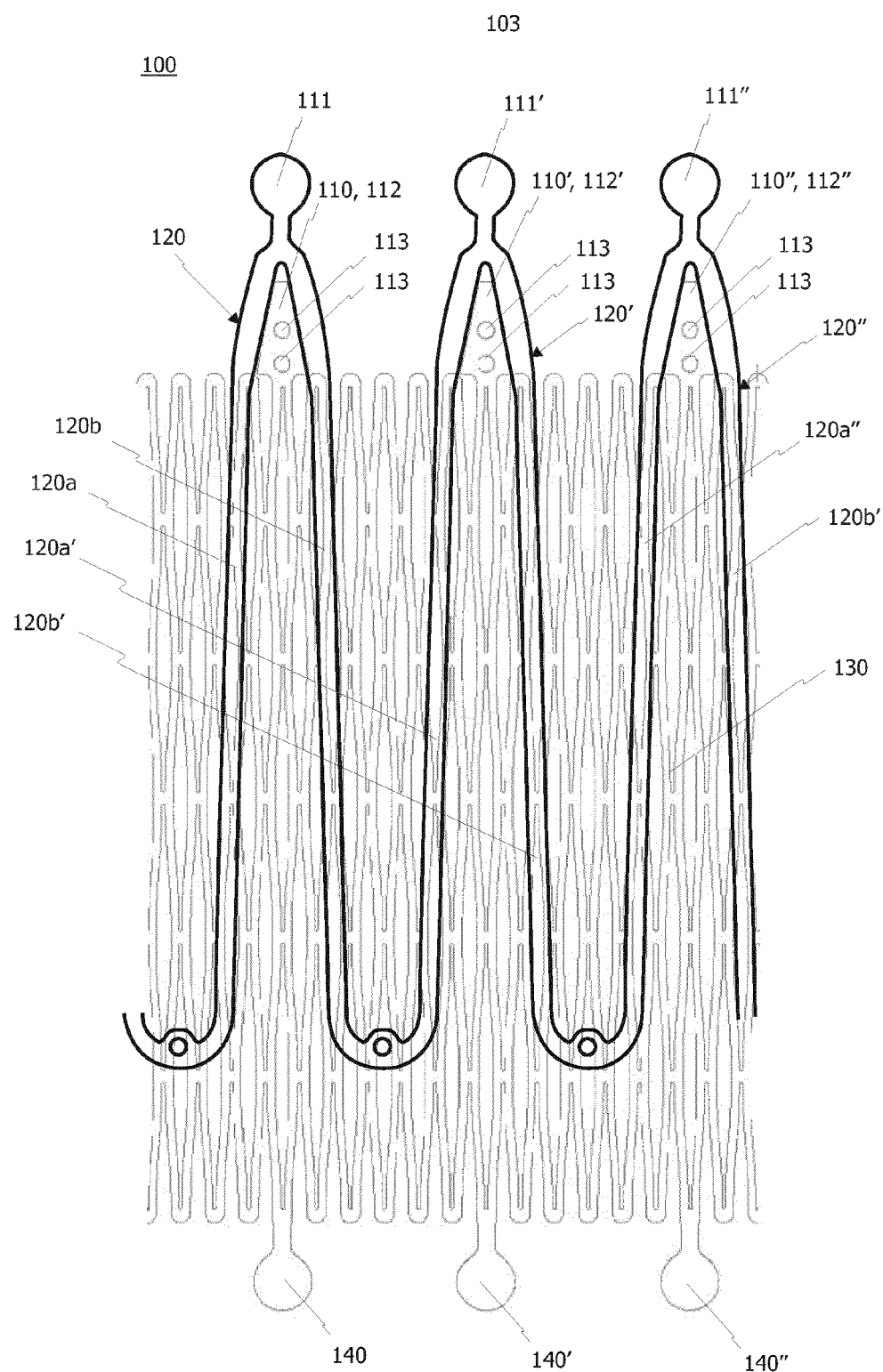

FIG. 4*a* a flat roll-out view of a cut out stent pattern without anchoring positioning arches, which can be used to manufacture a radially collapsible frame according to a second embodiment;

FIG. 4*b* a flat roll-out view of anchoring/positioning arches, which can be used to manufacture a radially collapsible frame according to a second embodiment;

FIG. 4*c* a flat roll-out view of a second embodiment of the inventive frame, comprising the cut out stent pattern of FIG. 4*a* and the anchoring/positioning arches of FIG. 4*a;*

Figure 5:
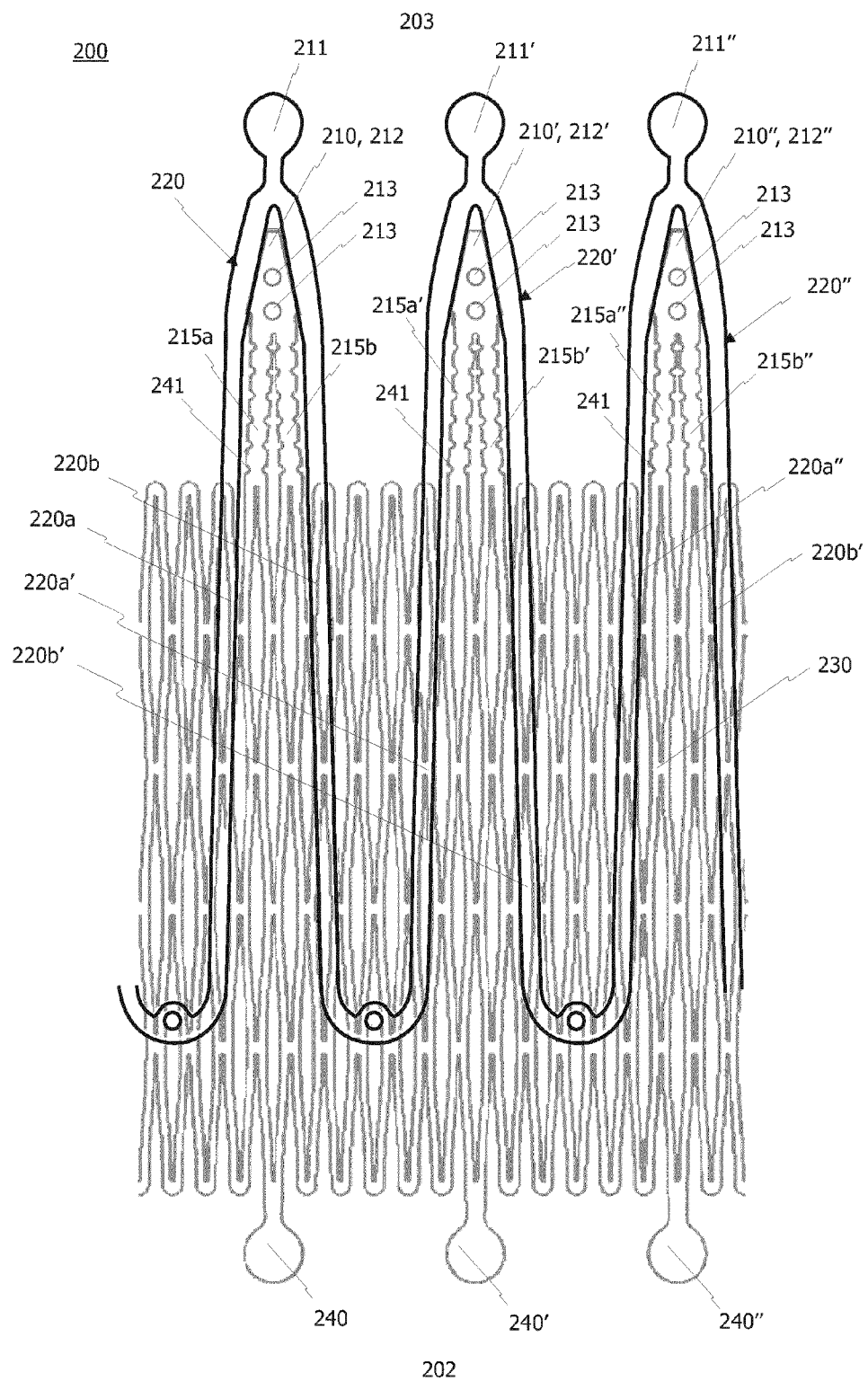

FIG. 5 a flat roll-out view of a third embodiment of the inventive radially collapsible frame.

FIGS. 1 and 2 show a first and second perspective view of a first embodiment of a radially collapsible frame 1 in accordance with the present invention. In this connection, it should be noted that FIGS. 1 and 2 respectively only show the depicted front half of the frame embodiment. In detail, the back half of the depicted frame which includes further commissure attachment regions and cell structures is not depicted in order to ease the understanding of the present invention.

The first embodiment of the inventive radially collapsible frame 1 depicted in FIGS. 1 and 2 comprises an outflow end region 3 at a proximal end of the frame and an inflow end region 2 at a distal end of the frame, opposite the outflow end region 3. If the present collapsible frame 1 is used as a supporting structure for an aortic heart valve replacement, for example, the outflow end region 3 is positioned towards the descending aorta, whereas the inflow end region 2 is located below the native valve annulus, that is, inside the left ventricle of the patient's heart.

As can further be seen from FIGS. 1 and 2, the radially collapsible frame further comprises at least two radially spaced commissure regions 10, 10', 10" located at the outflow region 3 of the frame 1. In the depicted embodiment the frame 1 comprises three radially spaced commissure regions, only two of which are depicted due to the fact that the back half is omitted from the respective side views. The commissure attachment regions 10 comprise a commissure attachment portion 12 which is configured to receive commissure edges of prosthetic valve leaflets of a valvular prosthesis. It should be noted that the valvular prosthesis is not shown in FIGS. 1 and 2 in order to improve the visibility of the structures of the inventive collapsible frame. In connection with the attachment of the commissure edges of the prosthetic valve leaflets, the attention is drawn to U.S. Pat. No. 6,460,382 B1, which shows various options for attaching a leaflet to the respective commissure attachment regions.

At the proximal end of the commissure attachment regions 10, 10', 10", retaining portions 11, 11', 11" are provided. The retaining portions 11, 11', 11" may comprise eyelets (not shown) which can be used in order to temporarily attach the inventive frame to a medical insertion device. Alternatively, the retaining portions could be received by grooves of a retaining element attached to the insertion device. The retaining portions 11, 11', 11" may comprise the depicted round shape. However, it is also conceivable to form the retaining portions 11, 11', 11" in any other shape, such as rectangular or polygonal shapes.

The radially spaced commissure attachment regions 10, 10', 10" are connected with each other by means of a cell structure 30 composed of a plurality of lattice cells 31, 31', 31", 32, 32', 32" which are arranged radially around a flow axis (not shown) of the frame 1. The flow axis of the inventive frame is basically defined by the longitudinal axis of the frame, around which all of the depicted frame structures are disposed circumferentially. As shown, the cell structure 30 is located beneath the radially spaced commissure attachment regions 10, 10', 10" and attached with the lower end of the commissure attachment portions 12, 12', 12". The commissure attachment portions 12, 12', 12" are designed so as to receive commissure edges of the leaflets of a valvular prosthesis. For this reason, the commissure attachment portions 12, 12', 12" comprise a plurality of fastening holes (FIG. 3), providing a means for suturing the valvular prosthesis to the frame 1.

The cell structure 30 may be used in order to attach the cusp edges of a valvular prosthesis to the frame. In the depicted embodiment, however, the cell structure 30 functions in order to protect the leaflets of the valvular prosthesis from any contact with the natural heart valve leaflets. In other words, the cell structure 30 may be used as a leaflet guard as will be described in more detail below.

Further to the cell structure 30 and the radially spaced commissure attachment regions 10, 10', 10", the inventive frame comprises at least one, in particular three, anchoring/positioning arches 20, 20', 20". The anchoring/positioning arches 20, 20', 20" radially overlap the cell structure 30 at least partially. In other words, the anchoring/positioning arches 20, 20', 20" are positioned at a radial distance from the flow axis, which is further than the radial distance of the cell structure 30 from the flow axis. That is, the anchoring/positioning arches 20, 20', 20" extend radially outwards relative to the cell structure 30.

Moreover, each of the positioning arches 20, 20', 20" comprises an eyelet 21, 21', 21" at a distal end thereof. The eyelets 21, 21', 21" may be used in order to carry radiopaque markers (not shown) that help with introducing the inventive frame into a patient's blood vessel.

Each of the at least one anchoring/positioning arches 20, 20', 20" is rigidly attached to two neighboring commissure attachment regions 10, 10', 10". According to the embodiment shown in FIGS. 1 and 2, the anchoring/positioning arches 20, 20', 20" are each formed integrally with two of the radially spaced commissure attachment regions 10, 10', 10" so as to form a single piece frame 1.

The first embodiment described by FIGS. 1 and 2 further comprises a plurality of circumferentially arranged retaining arches 40, 40', 40". Each of the retaining arches 40, 40', 40" comprises a first arm 40a, 40a', 40a" joined to a second arm 40b, 40b', 40b" at a distal end of the retaining arches 40, 40', 40". The two arms 40a, 40a', 40a", 40b, 40b', 40b" are joined by a rounded structure at the distal end, that is the direction of the inflow section 2 of the frame 1. It should be noted, however, that the retaining arches are completely optional and may be replaced by the cell structure 30 in further embodiments of the present invention.

The retaining arches 40, 40', 40" provide for a better support of the inventive frame 1 at the desired implantation site and provide for an attachment region for the cusp edge of the leaflets of the valvular prosthesis. In more detail, the cusp edge of a valvular prosthesis can be sutured to the respective arms 40a, 40a', 40a", 40b, 40b', 40b" of the retaining arches 40, 40', 40" by means of threads or wires. In order to improve the attachment of the valvular prosthesis with the arms 40a, 40a', 40", 40b, 40b', 40b" of the retaining arches 40, 40', 40" each of the arms 40a, 40a', 40a", 40b, 40b', 40b" may comprise a plurality of notches which are arranged substantially along substantially the hole range of the retaining arches 40, 40', 40". The notches 41 may further assist the flexibility of the retaining arches 40, 40', 40" and hence the retaining arches 40, 40', 40" can easily be adapted to the cusp edge of the prosthetic leaflets. In addition or as an alternative to the notches, the retaining arches 40, 40', 40" may be provided with a plurality of fastening holes, distributed along the retaining arms 40a, 40a', 40a", 40b, 40b', 40b".

Particularly shown in FIG. 1 is that the retaining arches 40, 40', 40" are circumferentially aligned with the positioning arches 20, 20', 20". This is because the native valve leaflets are preferably clamped between the positioning arches 20, 20', 20" and the retaining arches 40, 40', 40" respectively. For the same reason, the retaining arches 40, 40', 40" and the anchoring/positioning arches 20, 20', 20" have substantially the same shape, preferably a substantially U- or V-shaped structure.

Adjacent arms of two neighboring retaining arches 40, 40', 40" or positioning arches 20, 20', 20" merge at one of the commissure attachment regions 10, 10', 10", near the outflow end region 3 of the frame. Therefore, the retaining arches 40, 40', 40" and the positioning arches 20, 20', 20" are connected to each other near the outflow end region 3, particularly via the commissure attachment portions 12, 12', 12" of the commissure attachment regions 10, 10', 10".

As already mentioned above, the first and second arms 40a, 40a', 40a", 40b, 40b', 40b" of the retaining arches 40, 40', 40" intersect the cell structure 30 of the frame 1 according to the first embodiment. Due to this, the cell structure 30 comprises a first cell region 31 composed of a plurality of first cells, arranged between the respective first and second arms 40a, 40b, 40a', 40b', 40a", 40b" of each retaining arch 40, 40', 40" and a second cell region 32, composed of a plurality of second cells. In contrast to the first cells of the first cell region 31, the second cells of the second cell region 32 are arranged between adjacent arms of two neighboring retaining arches 40, 40', 40". One example of the second cells 32, 32', 32" can be derived from the perspective side view of FIG. 2. In this regard, the second cell region 32 is located between the first arm 40a of the first retaining arch 40 and the second arm 40b" of the third retaining arch 40".

Each of the first cells and/or second cells of the first and second cell region 31, 31', 31", 32, 32', 32" is formed by a plurality of struts 311, 321 which are connected with retaining arches 40, 40', 40" or each other respectively such that an onion-shaped cell structure is formed. The density of the first cell region 31, 31',31" is substantially equal to the density of the second cell region 32, 32', 32". Alternatively, it is also feasible to manufacture the frame 1 with first and second cell regions 31, 31', 31", 32, 32', 32" having different cell densities. In this regard, it is most preferable to construct the cell regions 31, 31', 31" in such a way that the density of the second cell region 32, 32', 32" is denser than the density of the first cell region 31, 31', 31".

The first and second cell regions 31, 31', 31" and 32, 32', 32" respectively have different functions in the depicted embodiment. The second cell region 32, 32', 32", on the one hand, provides for the requisite annular stability of the frame 1. The first cell region 31, 31', 31", which is arranged between the two arms 40a, 40a', 40a", 40b, 40b', 40b" of each respective retaining arm 40, 40', 40", on the other hand, is configured as a leaflet guard. That is, the first cell 31, 31', 31" region mainly stops the native heart valve leaflets from contacting the leaflets of the valvular prosthesis which can be attached to the inside of the frame 1. Of course, the first cell regions 31, 31', 31" also provides for some stability of the inventive frame 1.

FIGS. 1 to 3 further show that the inventive frame 1 may have at least one annular collar 50, which is connected to a lower part of the rounded structure, at the distal end section of each of the retaining arches 40, 40', 40". The annular collar 50 provides for an additional support of the frame 1 at the desired implantation site. In addition to the connection with the retaining arms 40, 40', 40" the annular collar 50 is connected to each or a few of the lower cells of the second cell region 32, 32', 32", which are arranged between adjacent arms 40a, 40a', 40a", 40b, 40b', 40b" of two neighboring retaining arches 40, 40', 40".

The annular collar 50 may constitute at least one flared and/or tapered section of the frame for improving fixation of the frame 1 in the position of the diseased valve of the patient and for preventing antegrade migration of the frame having a prosthetic valve affixed thereto. The embodiment shown in FIGS. 1 and 2 particularly shows that the struts 51 of the annular collar 50 are flared outwardly, so as to constitute a flared section of the frame 1. Another preferred alternative, however, is to construct the annular collar 50 in a substantial pear-shape. In more detail, the pear-shape is represented by a flared upper portion of the annular collar 50, which is connected to the cell structure 30 and the retaining arches 40, 40', 40" respectively, and a lower tapered section, which forms the inflow end 2 of the frame 1. In this way, the inflow end 2 of the frame 1 provides the stability of a flared section and is tapered inwardly in order to prevent forth stimulation of the nerves of the heart conduction system.

The particular flared and/or tapered shape of the annular collar 50 is preferably only visible in the expanded state of the frame 1, as can be derived from a comparison of FIGS. 2 and 3. Preferably, the flared or tapered section of the frame has a circular shape. However, according to anther embodiment, the annular collar 50 may only have flared or tapered sections provided near the location of the retaining arches and no flared or tapered sections near the regions in between the two arms of neighboring retaining arches 40, 40', 40". The annular collar 50 shown in FIGS. 1 and 2 is constructed of a plurality of struts formed in a rhomboidal shape.

FIG. 3 is a flat roll out view of the frame 1 according to the embodiment depicted in FIGS. 1 and 2. From FIG. 3 it is readily apparent that the frame 1 preferably exhibits a structure, which is integrally cut from a portion of a tube, in particular from a small metal tube. The small metal tube is preferably made of a shape memory material such as Nitinol. Of course, other shape memory materials are equivalently feasibly. FIG. 3 shows the flat roll out view of the frame 1 in its first collapsed mode. Of course, when the frame 1 is being introduced into the patient's body, it is transferred to its second expanded mode, which is illustrated by FIGS. 1 and 2. That is, the frame consists of a shape memory material such that the frame can transform from a temporary shape into a permanent shape under influence of an external stimulus. The temporary shape of the frame corresponds to the first compressed mode of the frame 1 (FIG. 3) and the permanent shape of the frame corresponds to the second expanded mode of the frame 1 (FIGS. 1 and 2).

The external stimulus can be a definable switching temperate bridge, which is preferably in the range of between room temperature and body temperature of the patient, so as to enable the frame 1 to expand as soon as the frame 1 gets in contact with the blood of the patient.

The present invention further relates to a method for manufacturing the radially collapsible frame 1. This method shall be described in more detail with reference to FIG. 3. Firstly a hollow tube made of shape memory material is provided and cut into the stent pattern shown in FIG. 3 by scanning a beam of laser radiation over the desired regions of the hollow tube. The cut out stent pattern of FIG. 3 shows a particularly important aspect, namely that the positioning arches 20, 20', 20" are formed above the cell structure 30, the commissure attachment regions 10, 10', 10" and the retaining arches 40, 40', 40" during the step for laser cutting. This is because, otherwise the positioning arches 20, 20', 20" could not be produced at the same time as the first cell region 31, 31', 31" of the cell structure 30.

After cutting the stent pattern by means of laser radiation, a shape-setting process is carried out in order to rearrange the direction of the anchoring/positioning arches 20, 20', 20". In this way, the final structure of the radially collapsible frame 1, shown in FIGS. 1 and 2 can be produced from a single piece of hollow tube. The shape-setting process includes a step for bending the anchoring/positioning arches 20, 20', 20" such that the at least one anchoring/positioning arch 20, 20', 20" extends in the same direction as the plurality of cells of the cell structure 30 or the retaining arches 40, 40', 40" respectively. In the depicted embodiment, the shape-setting process comprises a step for bending the anchoring/positioning arches 20, 20', 20" downward towards the inflow end 2 of the frame 1.

Bending the anchoring/positioning arches 20, 20', 20" downward towards the inflow 2 of the inventive frame may be implemented by applying a heat treatment process to the stent pattern. To this end, the stent pattern shown in FIG. 3 is deformed and fixed into the desired shape shown in FIGS. 1 and 2 of the present invention. Subsequently, the shaped stent pattern is heated to temperatures between 400° and 600° C. for several minutes and rapidly cooled down via water quenching or by means of rapid air cooling, for example. In this way, the frame 1 obtains a permanent mode, which is represented by FIGS. 1 and 2 of the present invention, and a temporary mode, which relates to the collapsed mode of the frame. Depending on the time and temperature of the heat treatment, the switching temperature between the temporary and the permanent mode of the frame 1 can be adjusted. According to the present invention, it is preferred to set the shifting temperature to a temperature between room temperature and body temperature of the patient, preferably about 22° C.

A second embodiment of the inventive radially collapsible frame can be derived from FIGS. 4a to 4c. The radially collapsible frame 100 according to the second embodiment is shown in a flat roll-out view in FIG. 4c. Similar to the first embodiment, the second embodiment of the inventive radially collapsible frame 100 comprises an outflow end region 103 at a proximal end of the frame 100 and inflow end region 102 at a distal end of the frame 100, opposite the outflow end region 103. The depicted radially collapsible frame 100 further comprises at least two radially space commissure region 110, 110', 110" located at the out flow end region 103 of the frame 100. In particular, the depicted frame 100 comprises three commissure regions 110, 110', 110". The commissure attachment regions 110, 110', 110" each comprise a commissure attachment portion 112, 112', 112" which is configured to receive commissure edges of prosthetic valve leaflet of a valve prosthesis.

The radially commissure attachment regions 110, 110', 110" are connected to each other by means of a cell structure which is composed of a plurality of lattice cells which are arranged around a flow axis (not shown) of the frame 100. As shown, the cell structure 130 is located between the radially spaced attachment regions 110, 110', 110" and attached with the lower end of the commissure attachment portions 112, 112', 112". The commissure attachment portions 112, 112', 112" comprise a plurality of fastening holes 113, providing a means for suturing the valvular prosthesis to frame 100. According to the second embodiment, the retaining portions 111, 111', 111" are not directly attached to the commissure attachment regions 110, 110', 110". Instead, as will be described in more detail below, the retaining portions 111, 111', 111" are attached to the anchoring/positioning arches 120, 120', 120" of the second embodiment.

Unlike the first embodiment, the inventive frame 100 according to the second embodiment does not comprise any retaining arches. For this reason, the cell structure 130 is used in order to attach the cusp edges of a valvular prosthesis to the frame 100. At the same time, the cell structure 130 of the second embodiment functions in order to protect the leaflets of the valvular prosthesis from any contact with the natural heart valve leaflets. That is, the cell structure 130 may be used as an attachment means and as a leaflet guard at the same time.

Further to the cell structure 130 and the radially spaced commissure attachment regions 110, 110', 110", the inventive frame 100 comprises at least one, in particular three, anchoring/positioning arches 120, 120', 120". The anchoring/positioning arches 120, 120', 120" radially overlap the cell structure 30 at least partially. In other words, the anchoring/positioning arches 120, 120', 120" are positioned at a radial distance at a flow axis, which is further than the radial distance of the cell structure 130 from the flow axis. That is, the anchoring/positioning arches 120, 120', 120" expand radially outwards relative to the cell structure 130. Each of the three anchoring/position arches 120, 120', 120" comprises two arms 120a, 120b, 120a', 120b', 120a", 120b" which are connected to each other at the inflow end 102 of the frame 100. In general, the anchoring/positioning arches exhibit the same features as the anchoring/positioning arches according to the first embodiment of the frame.

In contrast to the first embodiment, however, the positioning arches 120, 120', 120" of the second embodiment are not integrally formed together with the rest of the stent frame, such as the cell structure 130 and the commissure attachment region 110, 110', 110", shown in FIG. 4a. Rather, the anchoring/positioning arches 120, 120', 120" are manufactured as a separate piece, a roll-out view of which is shown in FIG. 4b. After producing the stent pattern of FIG. 4a and the anchoring/positioning arches 120, 120', 120" of FIG. 4b separately, the two parts are connected by means of welding, suturing, gluing or riveting. As can be derived from FIG. 4b, the anchoring/positioning arches 120, 120', 120" are most preferably welded to the edges of the commissure attachment regions 110, 110', 110" of the frame 100 according to second embodiment.

At the proximal end of the anchoring/positioning arches 120, 120', 120", retaining portions 111, 111', 111" are provided. The retaining portions 111, 111', 111" may comprise eyelets (not shown) which can be used in order to temporarily attach the inventive frame 100 to a medical insertion device. Alternatively, the retaining portions 111, 111', 111" could be received by grooves of a retaining element attached to the insertion device. The retaining portions 111, 111', 111" may comprise the depicted round shape. However, it is also conceivable to form the retaining portions 111, 111', 111" in any other shape, such as rectangular or polygonal shapes.

In order to manufacture the radially collapsible frame 100 of the second embodiment, it is not necessary to bend the anchoring/positioning arches 120, 120', 120" downward in a shape-setting process, after the stent pattern has been cut out of a hollow tube. Rather, the anchoring/positioning arches 120, 120', 120" are produced individually and attached in a separate manufacturing process step. This alternative manufacturing method has the advantage that no bending processes are introduced into the anchoring/positioning arches 120, 120', 120" during the shape setting process.

Finally it should be noted that the inventive frame 100 according to the second embodiment does not comprise a particular annular collar. Instead, the second embodiment of the inventive collapsible frame 100 comprises three additional support structures 140, 140', 140" as can be derived from FIGS. 4a and c. The additional support structures 140, 140', 140" are located at the inflow end region 102 of the radially collapsible frame 100 according to the second embodiment. Each of the three additional structures 140, 140', 140" is attached to a lower end of one of the plurality of the respective cells of the cell structure 130. Preferably, the additional support structure 140, 140', 140" are disposed radially around a flow axis of the frame 100 with an angle of about 120° in between two of the additional support structures 140, 140', 140". Furthermore, it can be derived from FIGS. 4a and 4c that the additional support structures 140, 140', 140" comprise a small rounded shape, so as to contact small areas of the heart valve ventricle below the natural heart valve annulus. Furthermore, the additional support structures 140, 140', 140" are preferably flared outward so as to achieve an effect, similar to the effect of the annular collar 40.

A third embodiment of the inventive radially collapsible frame is shown in FIG. 5. In more detail, FIG. 5 shows a flat roll-out view of the third embodiment of the inventive frame 200. The radially collapsible frame 200 according to the third embodiment mostly corresponds to the radially collapsible frame 100 of the second embodiment. The main difference between the frame 100 of the second embodiment and the frame 200 of the third embodiment is the construction of the cell structure 240. Unless stated otherwise, the parts of the frame 200 according to the third embodiment correspond identically to the parts of the frame 100 of the second embodiment. Similar parts were denoted with the reference signs of the second embodiment, wherein the factor "100" was added.

Compared to the cell structure 130 of the second embodiment, the cell structure 230 of the third embodiment comprises a smaller amount of lattice cells in the longitudinal direction of frame 200. In particular, the third embodiment shown in FIG. 5 does not comprise the uppermost row of cells of the cell structure 130 shown in FIG. 4c. Consequently, the frame 200 of the third embodiment has a smaller cell structure 130 which is compensated by a plurality of commissure attachment arms 215a, 215b, 215a', 215b', 215a", 215b". The commissure attachment arms 215a, 215b, 215a', 215b', 215a", 215b" are part of the commissure attachment regions 210, 210', 210" and configured to attach the commissure attachment portions 212, 112', 212' to the upper end of the cell structure 230. In particular, each of the commissure attachment portions 212, 212', 212" is attached to the cell structure 230 by means of two respective commissure attachment arms 215a, 215b, 215a', 215b', 215a", 215b".

Each of the commissure attachment arms 215a, 215b, 215a', 215b', 215a", 215b" comprises a plurality of notches 241, which have already been described with respect to the embodiment shown in FIGS. 1 to 3. Similar to the arms of the retaining arches according to the first embodiment, the commissure attachment arms 215a, 215b, 215a', 215b', 215a", 215b" are configured to assist with attaching the cusp edges of a valvular prosthesis to the collapsible frame 200. In particular, the cusp edges of the valvular prosthesis may be sutured to the notches 241 of the commissure attachment arches 215a, 215b, 215a', 215b', 215a", 215b".

All above mentioned and described embodiments and preferred embodiments will be appreciated by the skilled person to be workable also in other combinations of the features not explicitly described and such combinations will also be within the scope and disclosure of the invention. In particular, the frame of the first embodiment only optionally comprises retaining arches as depicted by the figures. Similar to the second and third embodiment, these retaining arches could be completely replaced by the cell structure, which could be used in order to attach the valvular prosthesis. Furthermore, the inventive frame could comprise more or fewer flared or tapered portions in its longitudinal direction. Finally, it should be noted that the frame is not restricted to the shape memory material Nitinol. Of course, any other suitable shape memory material is feasible especially in view of the bending stresses during the manufacturing as described above.

LIST OF REFERENCES 1, 100, 200 collapsible frame
2, 102, 202 inflow end region
3, 103, 203 outflow end region
10, 10', 10" commissure attachment regions
110, 110', 110"
210, 210', 210"
11, 11', 11" retaining portions
111, 111', 111"
211, 211', 211"
12, 12', 12" commissure attachment portion
112, 112', 112"
212, 212', 212"
20, 20', 20" anchoring/positioning arch
120, 120', 120"
20, 220', 220"
20a, 20a', 20a" first arm of anchoring/positioning arch
120a, 120a', 120a"
220a, 220a', 220a"
20b, 20b', 20b" second arm of anchoring/positioning arch
120b, 120b', 120b"
220b, 220b', 220b"
21, 121, 221 eyelet of positioning arches
30, 130, 230 cell structure
31, 31', 31" first cell region
32, 32', 32" second cell region
40, 40', 40" retaining arch
40a, 40a', 40a" first arm of retaining arch
40b, 40b', 40b" second arm of retaining arch
41, 241 notches
50 annular collar
51 struts of annular collar
113 fastening holes
140, 140', 140" additional support structure
240, 240', 240"
215a, 215a', 215a" first commissure attachment arm
215b, 215b', 215b" second commissure attachment arm
311 struts of first cell region
321 struts of second cell region

The invention claimed is:
1. A radially collapsible frame for a prosthetic valve, the frame comprising:
an outflow end region at a proximal end of the frame and an inflow end region at a distal end of the frame, opposite to the outflow end region;
at least two radially spaced commissure attachment regions located at the outflow end region of the frame and being configured to receive commissure edges of at least two prosthetic valve leaflets;
a plurality of circumferentially arranged retaining arches, each retaining arch including a first arm joined to a second arm at a distal end of the retaining arch;
a cell structure comprising a plurality of lattice cells proximal to the distal end of each retaining arch, the plurality of lattice cells comprising a plurality of first cells disposed between the first arm and the second arm of each retaining arch, and a plurality of second cells disposed between adjacent arms of two neighboring retaining arches; and
at least one anchoring/positioning arch radially outward of at least a portion of the plurality of first cells of the cell structure.
2. The frame according to claim 1, wherein the at least one anchoring/positioning arch is rigidly attached to the at least two radially spaced commissure attachment regions.
3. The frame according to claim 1, wherein the at least one anchoring/positioning arch is formed integrally with the at least two radially spaced commissure attachment regions as a single piece.
4. The frame according to claim 1, wherein the first arm and the second arm of each retaining arch are joined to one another at a connection having a substantially U-shaped or V-shaped structure.
5. The frame according to claim 1, wherein the at least one anchoring/positioning arch comprises three anchoring/positioning arches, and the plurality of retaining arches comprises three retaining arches.

6. The frame according to claim 1, wherein adjacent arms of two neighboring retaining arches merge at one of the at least two commissure attachment regions, near the outflow end region of the frame.

7. The frame according to claim 1, wherein each of the first cells or each of the second cells, or each of the first cells and each of the second cells, is formed by a plurality of struts.

8. The frame according to claim 1, wherein each of the anchoring/positioning arches and each of the retaining arches includes a closed end, and wherein the closed end of each anchoring/positioning arch is substantially circumferentially aligned with the closed end of one of the retaining arches.

9. The frame according to claim 1, wherein at least one retaining arch of the plurality of retaining arches comprises at least one fastening portion including a plurality of fastening holes configured to receive a suture.

10. The frame according to claim 9, wherein the at least one fastening portion further includes a plurality of notches configured to receive a suture.

11. The frame according to claim 1, wherein the frame further comprises at least one annular collar connected to distal end sections of the first and second arms of the retaining arches.

12. The frame according to claim 11, wherein the at least one annular collar is connected to struts that form the second cells of the plurality of second cells.

13. The frame according to claim 11, further comprising a plurality of eyelets uniformly distributed around a lower end section of the at least one annular collar for fixing a prosthetic valve to the frame.

14. The frame according to claim 11, wherein, in an expanded state of the frame, a lower end section of the at least one annular collar constitutes a flared or tapered section of the frame.

15. The frame according to claim 1, wherein, in an expanded state of the frame, an inflow end region of the frame is flared or tapered.

16. The frame according to claim 15, wherein the inflow end region of the frame has a circular cross-section.

17. The frame according to claim 16, wherein regions in between adjacent arms of two neighboring retaining arches are not tapered or flared.

18. The frame according to claim 1, wherein the frame has a scalloped inflow edge when the frame is in an expanded state.

19. The frame according to claim 1, wherein the frame is integrally cut from a portion of a tube.

20. The frame according to claim 1, wherein the frame includes a first collapsed mode for introduction into a patient's body and a second expanded mode for implantation.

21. The frame according to claim 20, wherein the frame comprises a shape memory material, such that the frame is configured to transform from the first collapsed mode into the second expanded mode under influence of an external stimulus.

22. The frame according to claim 21, wherein the external stimulus is a temperature between room temperature and 37° C.

23. The frame according to claim 1, wherein the at least one anchoring/positioning arch is configured to be positioned within a pocket of a native cardiac heart valve and positioned on a first side of a plurality of native heart valve leaflets, and wherein the plurality of retaining arches is configured to be positioned on a second side of the plurality of native heart valve leaflets opposite the first side.

24. The frame according to claim 1, wherein the at least one anchoring/positioning arch includes a substantially U-shaped or V-shaped structure.

25. An endoprosthesis comprising a radially collapsible frame according to claim 1 and a valvular prosthesis attached to an inner surface of the frame.

26. The endoprosthesis according to claim 25, wherein the valvular prosthesis is made from pericardium, and wherein in an expanded state of the frame, the respective arms of the retaining arches have a shape that matches a plurality of leaflets of the valvular prosthesis attached to the frame.

27. A radially collapsible frame for a prosthetic valve, the frame comprising:
at least two commissure attachment regions at a proximal, outflow end of the frame;
a plurality of circumferentially arranged retaining arches, each retaining arch including a first arm joined to a second arm in an apex pointing towards a distal, inflow end of the frame;
a cell structure comprising a plurality first cells between the first arm and the second arm of each retaining arch, and a plurality of second cells between adjacent arms of two neighboring retaining arches, the plurality of first cells including at least two first cells arranged in a row between the first arm and the second arm of each retaining arch; and
at least one anchoring/positioning arch radially outward of at least a portion of the cell structure.

* * * * *